United States Patent [19]

Gustafson et al.

[11] Patent Number: 5,413,939
[45] Date of Patent: May 9, 1995

[54] SOLID-PHASE BINDING ASSAY SYSTEM FOR INTERFEROMETRICALLY MEASURING ANALYTES BOUND TO AN ACTIVE RECEPTOR

[75] Inventors: Eric K. Gustafson, Palo Alto; Jimmy D. Allen, Cupertino; Michael E. Cobb, San Jose, all of Calif.

[73] Assignee: First Medical, Inc., Mountain View, Calif.

[21] Appl. No.: 86,345

[22] Filed: Jun. 29, 1993

[51] Int. Cl.$^6$ ............ G01N 33/543; G01J 1/20
[52] U.S. Cl. ............ 436/518; 436/501; 436/524; 436/527; 436/531; 435/970; 250/201.9
[58] Field of Search ............ 318/593, 640; 356/317–318, 361, 128, 244; 372/32, 29; 385/12, 14; 422/55, 57, 62; 435/7.92–7.95, 970; 436/501, 518, 527, 524, 531, 805; 250/201.9, 208.2

[56] References Cited

U.S. PATENT DOCUMENTS

| | | | |
|---|---|---|---|
| Re. 33,581 | 4/1991 | Nicoli et al. | 435/7.2 |
| 3,639,558 | 2/1972 | Csizmas et al. | 424/12 |
| 3,823,604 | 7/1974 | Burch et al. | 73/71.3 |
| 3,853,467 | 12/1974 | Giaever | 23/230 B |
| 3,854,050 | 12/1974 | Peterson et al. | 250/429 |

(List continued on next page.)

FOREIGN PATENT DOCUMENTS

| | | | |
|---|---|---|---|
| 3506703C1 | 4/1986 | Germany | 435/6 |
| 2197068A | 5/1988 | United Kingdom . | |
| WO88/02118 | of 1988 | WIPO | 436/526 |
| WO88/00696 | 1/1988 | WIPO | 422/82.01 |
| WO90/09576 | 8/1990 | WIPO | 436/518 |
| WO91/04483 | 4/1991 | WIPO | 436/518 |
| WO91/04489 | 4/1991 | WIPO | 436/518 |
| WO91/04491 | 4/1991 | WIPO | 436/518 |
| WO91/13353 | 5/1991 | WIPO | 436/518 |
| WO92/06379 | 4/1992 | WIPO | 436/518 |
| WO92/14136 | 8/1992 | WIPO | 436/518 |

OTHER PUBLICATIONS

Van Nostrand's Scientific Encyclopedia, seventh edition, (1989), pp. 1579–1580, "Interferometer".
Alex Abramovici et al., "LIGO: The Laser Interferometer Gravitational-Wave Observatory", Science, vol. 256, 17 Apr. 1992, pp. 325–333.
M. A. Butler, "Optical fiber hydrogen sensor", Appl. Phys. Lett. 45(10), 15 Nov. 1984, ©1984 American Institute of Physics, pp. 1007–1009.
"The Electronic Toolbox Part 1", Analytical Chemistry, vol. 57, No. 11, Sep. 1985, ©1985 American Chemical Society, pp. 1188A–1202A.

Primary Examiner—Carol A. Spiegel
Attorney, Agent, or Firm—Townsend and Townsend Khourie and Crew

[57] ABSTRACT

A solid-phase binding assay that measures interferometrically either antibodies or binding pair antigens bound to a spinning disc on which the complementary antigen or antibody has previously been coated in an alternating pattern of immunologically active and inactive spots. The spinning disc is inserted into one arm of a Mach-Zehnder interferometer and as the disc spins the bound and unbound spots pass one after another through the two light beams causing a periodic phase shift in the light. These phase modulated light beams are then recombined at a beam-splitter converting the phase modulation into an amplitude modulation. The two recombined beams then fall on a photodetector which converts the periodically varying optical power into a periodically varying electrical current whose amplitude is proportional to the amount of bound protein on the surface of the disc and whose modulation frequency is equal to the frequency with which the spots pass through the light beam. If the disc is spinning rapidly and there are many spots around the disc this signal frequency will be much higher than the frequency of the noise due to the disc wobble and the vibrations imparted to the interferometer by the spinning motor.

17 Claims, 10 Drawing Sheets

U.S. PATENT DOCUMENTS

| | | | |
|---|---|---|---|
| 3,926,564 | 12/1975 | Giaever | 23/259 |
| 3,939,350 | 2/1976 | Kronick et al. | 205/365 |
| 3,960,451 | 6/1976 | Wirz et al. | 356/161 |
| 3,960,488 | 6/1976 | Giaever | 23/230 B |
| 3,960,489 | 6/1976 | Giaever | 23/230 B |
| 3,960,490 | 6/1976 | Giaever | 23/230 B |
| 3,960,491 | 6/1976 | Giaever | 23/230 B |
| 3,975,238 | 8/1976 | Bean et al. | 195/103.5 R |
| 3,979,184 | 9/1976 | Giaever | 23/253 TP |
| 3,979,509 | 9/1976 | Giaever | 424/12 |
| 4,011,308 | 3/1977 | Giaever | 424/1.5 |
| 4,018,886 | 4/1977 | Giaever | 424/12 |
| 4,030,835 | 6/1977 | Firester et al. | 356/111 |
| 4,050,895 | 9/1977 | Hardy et al. | 23/230 R |
| 4,054,646 | 10/1977 | Giaever | 424/12 |
| 4,090,849 | 5/1978 | Healy et al. | 23/253 TP |
| 4,115,535 | 9/1978 | Giaever | 424/1 |
| 4,172,827 | 10/1979 | Giaever | 260/112 R |
| 4,181,501 | 1/1980 | Keese et al. | 23/230 B |
| 4,223,257 | 9/1980 | Miller | 318/594 |
| 4,321,057 | 3/1982 | Buckles | 23/230 B |
| 4,399,099 | 8/1983 | Buckles | 422/58 |
| 4,451,923 | 5/1984 | Hansch et al. | 372/32 |
| 4,487,839 | 12/1984 | Kamentsky | 436/518 |
| 4,508,832 | 4/1985 | Carter et al. | 436/517 |
| 4,521,522 | 6/1985 | Lundstrom et al. | 436/525 |
| 4,537,861 | 8/1985 | Elings et al. | 436/518 |
| 4,554,088 | 11/1985 | Whitehead et al. | 252/62.54 |
| 4,558,012 | 12/1985 | Nygren et al. | 436/501 |
| 4,608,344 | 8/1986 | Carter et al. | 436/34 |
| 4,628,037 | 12/1986 | Chagnon et al. | 436/526 |
| 4,647,544 | 3/1987 | Nicoli et al. | 436/518 |
| 4,695,392 | 9/1987 | Whitehead et al. | 252/62.54 |
| 4,695,393 | 9/1987 | Whitehead et al. | 252/62.54 |
| 4,698,302 | 10/1987 | Whitehead et al. | 435/94 |
| 4,818,710 | 4/1989 | Sutherland et al. | 436/527 |
| 4,820,649 | 4/1989 | Kawaguchi et al. | 436/501 |
| 4,844,613 | 7/1989 | Batchelder | 356/318 |
| 4,876,208 | 10/1989 | Gustafson et al. | 436/531 |
| 4,886,761 | 12/1989 | Gustafson | 436/518 |
| 4,931,384 | 6/1990 | Layton et al. | 435/7 |
| 4,932,783 | 6/1990 | Kersey et al. | 356/345 |
| 4,940,328 | 7/1990 | Hartman | 356/345 |
| 4,950,074 | 8/1990 | Fabricius et al. | 356/133 |
| 5,089,387 | 2/1992 | Tsay et al. | 435/6 |
| 5,096,807 | 3/1992 | Leaback | 435/6 |
| 5,118,608 | 6/1992 | Layton et al. | 435/7.1 |
| 5,120,131 | 6/1992 | Lukosz | 356/351 |
| 5,126,276 | 6/1992 | Fish et al. | 436/531 |
| 5,173,747 | 12/1992 | Boiarski et al. | 356/361 |
| 5,196,350 | 3/1993 | Backman et al. | 436/501 |
| 5,218,419 | 6/1993 | Lipson et al. | 356/345 |
| 5,225,887 | 7/1993 | Lipson et al. | 356/345 |

SOLID-PHASE BINDING ASSAY SYSTEM FOR INTERFEROMETRICALLY MEASURING ANALYTES BOUND TO AN ACTIVE RECEPTOR

BACKGROUND OF THE INVENTION

This invention relates to a solid-phase binding assay system for measuring analytes.

Many solid-phase immunoassays involve surface illumination and consequent light emissions from molecules attached to the surface. Generally, these emissions travel in all directions. Either these divergent emissions must be collected with expensive and awkward light collection optics to achieve high sensitivity or the inherent inefficiencies and consequent low signal to noise ratio must be accepted.

Many immunoassay systems have been developed using different physically measurable properties of reagents to provide a measurement of an analyte concentration. Radio immunoassay (RIA), immunofluorescence, chemiluminescence, enzyme immunoassays (EIA), free radical immunoassays (FRAT), light scattering nephelometry, transistor bridge probes, indium reflective surfaces, and ultrasonic probes have been applied. These systems use the highly selective reaction between a primary binding reagent material such as an antibody or antigen and an analyte selectively binding therewith.

An attempt by others to develop an optical probe comprising a metal covered diffraction grating coated with a monoclonal antibody specific for a virus, bacterium or other desired antigen has been described by Moffatt, A. *Genetic Engineering News,* p. 18, October 1986. The shift in wavelength of reflected light is apparently determined and correlated to a concentration in analyte.

A reflectance method for quantification of immunological reactions on polished crystalline silicon wafer surfaces has been described by Arwin, H. et al, *Analytical Biochemistry,* 154:106–112 (1985). Indium surface reflection methods are described by Giaver in U.S. Pat. Nos. 3,853,467, 3,926,564, 3,960,488, 3,960,489, 3,960,490, 3,975,238, 3,979,184, 3,979,509, 4,011,308, 4,018,886, 4,054,646, 4,115,535, 4,172,827 and 4,181,501. Liquid layer thicknesses can be monitored by a reflectance method described in U.S. Pat. No. 3,960,451.

Biosensors such as field effect transistors probes and their use in assays are described by Pace, S., *Medical Instrumentation,* (19(4):168–172 (1985). Polysilicon surfaces are included among the possible biosensor surfaces to which primary binding reagents can be attached.

Other patents of interest include U.S. Pat. Nos. 4,537,861; 4,558,012; 4,647,544; 4,820,649; 4,876,208; 4,886,761; 5,089,387; 5,120,131; 5,196,350; and RE 33,581.

The most sensitive instrument for the measurement of optical phase shift due to physical displacement or refractive index change or both is the optical interferometer. There are many different interferometer designs. Measurements made with interferometers include: 1) the attempt to detect gravitational radiation (A. Abramovici, et al. "LIGO: The Laser Interferometer Gravitational-Wave Observatory" Science 256, Apr. 17, 1992, p. 325), 2) positioning of the cutting head and work piece in precision machining (C. Evans, "Precision Engineering: an Evolutionary View", Cranfield Press 1989), 3) tectonic plate movement in geology for earthquake prediction (P. L. Bender, "Laser Measurement of Long Distances", Proc. IEEE, Vol. 55, No. 6, June 1967, PP. 1039–1045) and 4) microarcsecond astrometry (R. D. Reasenberg, et al. "Microarcsecond Optical Astrometry: An Instrument and its Astrophysical Applications", The Astronomical Journal, 96 (5) 1988).

SUMMARY OF THE INVENTION

The present invention provides a new and improved binding assay technique (apparatus and method) for measuring analytes having improved sensitivity by which it is possible to measure molecules at low solution concentration. The system is characterized by high linearity and does not require labeling, although labeling may be advantageously employed under certain circumstances. Further, the technique has a large dynamic range, i.e., is capable of measuring over many orders of magnitude in solution concentration without requiring changes in the disposable surface concentration or reagent concentration changes. In other words for a given test only one disposable reagent set should be necessary.

Additionally the technique produces a background free output such that when no analyte exists in the incubating solution, very little or no signal results. The technique involves few process steps, can be used with short incubation times, and has low coefficient of variation in relation to a standard measurement.

According to a broad aspect of the present invention, a substrate is provided with at least one active binding reagent region, and a change in optical path length due to binding of an analyte is measured. This is preferably done by comparing the phase of light that has passed through the active binding reagent region with the phase of light that has not. The phase comparison is preferably performed with an interferometer.

In one set of embodiments, the novel solid-phase binding assay system interferometrically measures analytes, e.g., antibodies, antigens and other target substances that can be specifically bound to an analyte receptor region, and includes a rotating disc having the analyte receptor region comprising an alternating pattern of immunologically active and inactive portions, which may be formed as wedges or spots. The spinning disc is inserted into one arm of a two beam interferometer such as the Mach Zehnder or Michelson interferometer. As the disc spins, bound and unbound portions of the analyte receptor region (resulting from specific binding of the analyte to the active portions of the analyte receptor region) pass one after another through the laser beam causing a periodic phase shift in the light. This phase modulated light beam is recombined with the beam from the other interferometer arm (which experiences no periodic phase modulation), converting the phase modulation into an amplitude modulation.

The two recombined beams then fall on a photodetector which converts the periodically varying optical power into a periodically varying electrical current. The amplitude of this current is proportional to the amount of bound analyte on the active regions of the disk and the frequency of the current variation is the frequency at which the active regions pass through the laser beam. If the disc is spinning rapidly and there are many binding portions (e.g., wedges or spots), around the disc, this signal frequency will be much higher than the frequency of the noise due to the disc wobble, the variation in the disc thickness, and the vibrations imparted to the interferometer by the spinning motor.

In other embodiments, the disc would not be rotated, but the beam would be expanded so that a large number of spots on the disc could be interrogated at one time.

A further understanding of the nature and advantages of the present invention may be realized by reference to the remaining portions of the specification and the drawings.

DESCRIPTION OF THE PREFERRED EMBODIMENTS

Figure 1A:
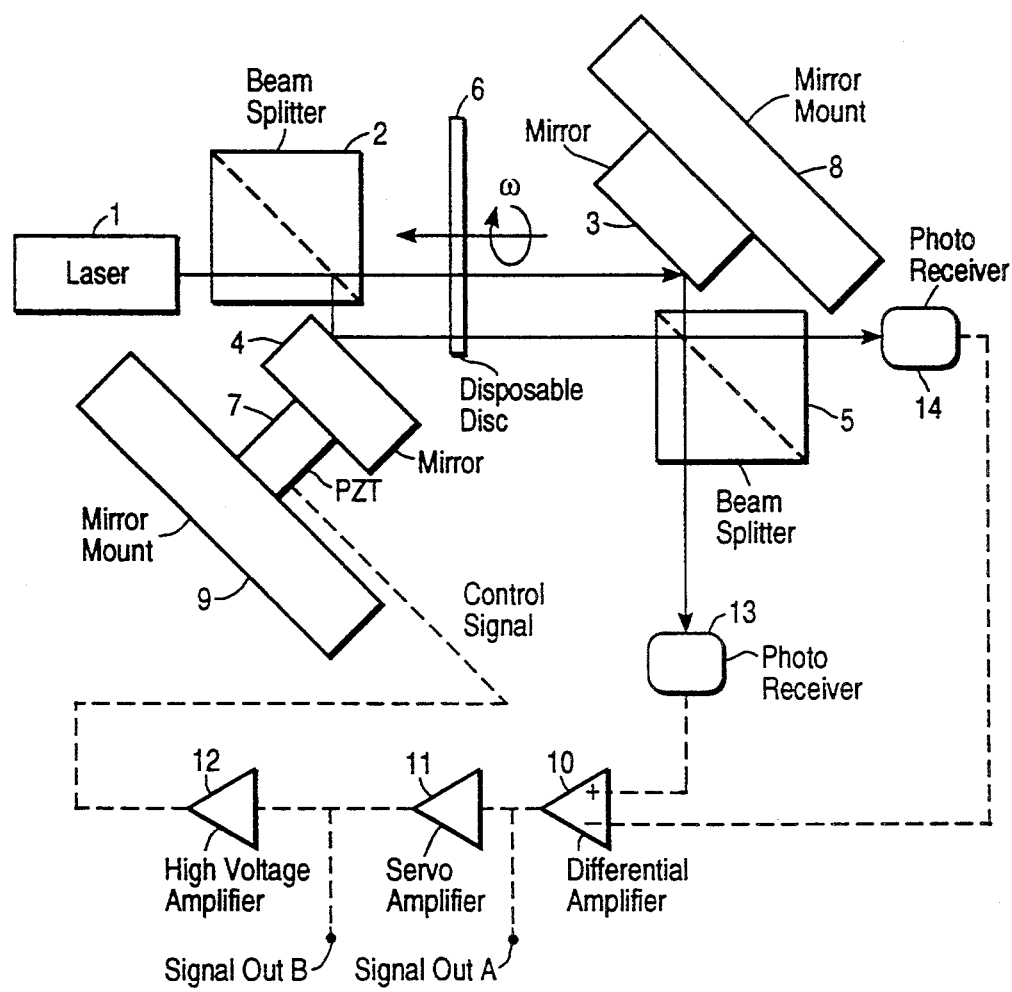
FIG. 1A is a schematic block diagram of a first embodiment of the system of the present invention, employing a Mach-Zehnder interferometer.

The present invention is useful in assaying for a wide variety of analytes in virtually any type of sample which is liquid, which can be liquified, or which can be suspended in a liquid. The method and kit will find their greatest use with biological specimens, such as blood, serum, plasma, urine, cerebral fluid, spinal fluid, ocular lens liquid (tears), saliva, sputum, semen, cervical mucus, scrapings, swab samples, and the like. Use will also be found with industrial, environmental and food samples, such as water, process streams, milk, meat, poultry, fish, conditioned media, and the like. Under certain circumstances, it may be desirable to pretreat the sample, such as by liquefaction, separation, dilution, concentration, filtration, chemical treatment, or a combination thereof, in order to improve the compatibility of the sample, with the remaining steps of the assay. The selection and pretreatment of biological, industrial, and environmental samples prior to immunological testing is well known in the art and need not be described further.

The analyte to be detected may be virtually any compound, composition, aggregation, or other substance which may be immunologically or otherwise detected. That is, the analyte, or portion thereof, will usually be antigenic or haptenic having at least one determinant site, or will be a member of a naturally-occurring binding pair, e.g., enzyme and substrate, carbohydrate and lectin, hormone and receptor, complementary nucleic acids, and the like. Analytes of particular interest include antigens, antibodies, proteins, carbohydrates, haptens, drugs, hormones, hormone metabolites, macromolecules, toxins, bacteria, viruses, enzymes, tumor markers, nucleic acids, and the like, although other types of substances may also be detected. A non-exhaustive list of exemplary analytes is set forth in U.S. Pat. No. 4,366,241, at column 19, line 7 through column 26, line 42, the disclosure of which is incorporated herein by reference.

Presence of the analyte in the sample will be measured by detecting specific binding between the analyte and an anti-analyte covalently or non-covalently bound to a surface on a solid phase support, usually a disk as described in detail hereinafter.

The anti-analyte will be a specific binding substance capable of binding directly or indirectly to the analyte with a high affinity, typically being at least about $10^8$ $M^{-1}$, usually being at least about $10^9$ $M^{-1}$, and sometimes being $10^{10}$ $M^{-1}$ or greater. The anti-analyte should be free from cross-reactivity with other substances that may be present in the sample or the assay reagents. Most commonly, the anti-analyte will be a monoclonal or polyclonal antibody raised against the analyte, but in some cases it may be possible to employ natural receptors for biological analytes, as described above. In cases where the analyte is itself an antibody, it will of course be possible to employ antigens or haptens recognized by the antibody as the anti-analyte.

While the anti-analyte will most often bind directly to the analyte, the present invention also comprises indirect binding of anti-analyte to analyte, i.e., the use of one or more intermediate binding substances to sequester or effect a linkage to the analyte. For example, when binding to a solid phase, it will be possible to provide a primary binding substance, e.g., avidin or a primary antibody, on the solid phase which is able to bind directly a soluble substance which is specific for the analyte, e.g., a biotinylated antibody or secondary antibody which recognizes the analyte. A wide variety of such indirect binding protocols are available and well described in the scientific and patent literature. The term "anti-analyte" as used in the specification and claims are thus intended to include all substances which are able to bind the analyte, either directly (i.e., without an intermediate binding substance) or indirectly (i.e., with one or more intermediate binding substances forming a linkage).

The apparatus and methods of the present invention will often advantageously employ amplified binding systems where capture of a single analyte molecule on the solid phase surface will result in binding of at least one additional molecule, particle, or the like, to increase the total amount and/or thickness, of material which is bound to the analyte-specific portion of the analyte-specific portion of the analyte receptor region. In this way, the sensitivity of analyte detection can be increased without any need to modify the system hardware. Suitable immunological amplification techniques are well described in the patent and scientific literature. See, for example, U.S. Pat. Nos. 4,463,090; 4,687,736; and 4,595,655, the full disclosures of which are incorporated herein by reference. Other preferred techniques of the present invention will provide for binding of a dense marker particle, such as a gold particle, to the analyte-specific portion of the analyte receptor region. Such dense particles will significantly enhance detectability using the interferometer systems described hereinafter.

The term "binding reagent" is used herein to designate one member of any binding pair of compounds or materials which selectively bind to form a conjugate. The members of the binding pair are generically denoted by the terms "ligand" and "antiligand" either one of which can be a binding reagent. The binding reagent can be a member of the well-known immunological pairs (MIPs) such as antibody-antigen or antibody-hapten pairs wherein the antibody binds selectively with the respective antigen or hapten, or combinations where the antibody is replaced with an Fab, Fab' F(ab')2 fragment or hybrid antibody. The binding reagent can also be a member of other types of binding pairs such as biotin-avidin; apo-protein:cofactor; lectin-saccharide (or polysaccharide); lectin-cell; IgG antibody Fc portion with protein A or protein G; enzyme-enzyme substrate; sense-antisense nucleic acid sequences such as DNA:DNA, RNA:RNA; DNA:RNA, DNA fragments or other nucleic acid sequences; enzyme-enzyme inhibitor; receptor-ligand; protein-protein receptor; protein subunit-protein subunit; lipid-lipid, one or both members including a detergent, liposome, membrane, etc.; (metal) ion-ionophore; chelating agent-metal ion; virus-antibody; Mycoplasmatales or mycoplasmatales fragment-antibody; spore or spore fragment-antibody; parasite or parasite fragment-antibody; yeast or yeast fragment-antibody; cell-antibody; hapten labeled entity-antibody; receptor-ligand; cell receptor-cell; nucleic acid probe-"target"; binding pairs where one or both binding members are elements of any self assembling structure including, but not limited to oligomeric protein subunits, nucleic acid sequences, virus components (protein, nucleic acid, lipid), crystal monomers, organelle components; and the like. Also included are specific binding pairs wherein a mercapto group binds specifically with a dithio or disulfide group (—S—SH or —S—S—) or with a N-substituted-2,4-diketo-3-pyrroline group, and other molecules with functional groups that will bind each other specifically. In general, the binding reagent is selected to bind specifically or selectively with the analyte, the material for which a sample is assayed.

The term "binding pair" is also intended to include compound or complexes of any of the above listed members of a binding pair coupled with other or with any of a variety of "labels": (typically those of large mass) including particles such as latex, metal sol, cell., enzyme, polymer, etc.; any of the above listed members of a binding pair coupled with an entity which can generate an accumulation of mass such as enzyme generating a precipitate, product, or crystal nucleus, for example, or a light sensitive material generating a solid accumulation such as silver; anything that permits cell attachment and/or growth such as cell receptors, collagen, fibrin, fibronectin and the like; or anything that promotes loss of mass such as enzymes, radiation, acids, bases, corrosives, etching agents, ionizing radiation, X-rays, vibration (ultrasound); and the like.

The term "binding assay", is used herein to designate an assay using any binding reaction between a binding reagent and the other member of the binding pair which is selectively bindable therewith.

The term "alkyl", as used herein includes saturated and unsaturated, straight, branch-chained and cyclic hydrocarbon groups. The term "lower alkyl" is defined to include alkyl groups having from 1 to 6 carbon atoms.

I. Interferometer

Referring now to the drawings, wherein like reference numerals designate identical or corresponding parts throughout the several views, and more particularly to FIG. 1A thereof, an interferometric immunosensor in the Mach-Zehnder configuration is shown. Interferometers operate by comparing the phase difference between two light waves that have originated from a single source and have been separated to travel over different paths. The difference in phase is then read out by recombining the beams, thus converting this phase difference to an amplitude difference. Ultimately the amplitude is determined by measuring the optical power in the recombined beam. The Mach-Zehnder interferometer sensor configuration shown in FIG. 1A includes a laser 1, a first 50/50 beamsplitter 2, a mirror 3, a mirror 4, a second 50/50 beamsplitter 5, a piezoelectric displacement transducer (PZT) 7, a mirror mount 8, a mirror mount 9, a differential amplifier 10, a servo amplifier 11, a high voltage amplifier 12, and photoreceivers 13 and 14. The upper beam will be referred to as the signal beam and the lower beam the reference beam. A spinning disc 6 is disposed in at least one of the beams.

In the Mach-Zehnder geometry the light output from laser 1 passes through beamsplitter 2 where it is split into two equal power beams: the reference beam and the signal beam. The reference beam is reflected from mirror 4 and then passes through disposable disc 6 to beamsplitter 5. The signal beam passes through the spinning disposable disc and is then reflected from mirror 3 and into beamsplitter 5 where it is recombined with the reference beam. The recombined reference and signal beams are passed to photoreceivers 13 and 14, the outputs of which are applied to differential amplifier 10. The output of differential amplifier 10 is applied to servo amplifier 11, the output of which is applied to high voltage amplifier 12 which drives a piezoelectric transducer (PZT). PZT 7 moves mirror 4 back and forth until the path length difference between the two beams corresponds to a phase shift where exactly half of the light falls on photoreceiver 13 and half falls on photoreceiver ].4. Each photoreceiver consists of a photodiode and a transimpedance amplifier, as described in more detail below. The voltage output of the photoreceiver is compared to a reference voltage and this difference provides an error signal that can be used to control the position of mirror 4 with the PZT 7. The servo amplifier 11 provides gain and phase control and limits the bandwidth of the error signal. The high voltage amplifier 12 amplifies the error signal up to the high voltage (usually a few hundred volts) required to move the PZT displacement transducer 7.

Next computed is the optical power at photoreceivers 13 and 14. The electric field at photoreceiver 13 is equal to the coherent superposition of the field from the two paths through the interferometer. The laser beam output power is $P_o$ and the electric field is $E_o$. The field that passes through the beamsplitter is $$\frac{E_o}{\sqrt{2}}$$

The reason for the root 2 rather than simply dividing by 2 is that the beamsplitter divides the power in half and the power is proportional to the square of the absolute value of the electric field. The field that is reflected from the beamsplitter is $$i\frac{E_o}{\sqrt{2}}$$

The i is included because there is a 90 degree phase difference between the reflected and the transmitted beams. Now these two beams are recombined on the second beamsplitter and the first field becomes after transmission through the beamsplitter $$\frac{E_o}{2} e^{i\phi_1}$$

and the second field becomes after reflection from the beamsplitter $$-\frac{E_o}{2} e^{i\phi_2}$$

Figure 1B:
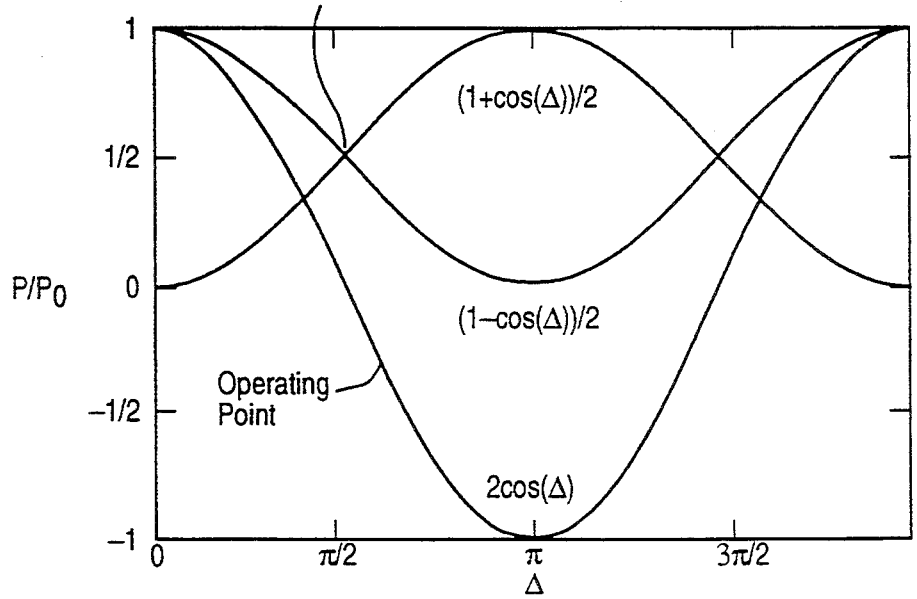
FIG. 1B is a graph indicating signals produced in the interferometer of FIG. 1A and illustrating a preferred operating point.

The electric field at photoreceiver 13 is then the sum of these two fields and similarly for the electric field at photoreceiver 14.

$$E_{13} = \frac{E_0}{2} [e^{i\phi_1} - e^{i\phi_2}]$$

$$E_{14} = \frac{E_0}{2} e^{i\pi/2} [e^{i\phi_1} + e^{i\phi_2}]$$

where $\phi_1$ and $\phi_2$ are the total phases accumulated in the signal and reference paths. The reason for the sign change between the field on photoreceiver 13 and photoreceiver 14 is that the two paths through the interferometer to photoreceiver 14 have each beam reflecting once and transmitting once through a beamsplitter while for photoreceiver 13 one path only transmits and the other path only reflects from a beamsplitter. To compute the optical power on the detectors, the absolute square of the electric fields is integrated over the area of the photoreceivers. If the laser beam is much smaller than the detector area this becomes $$P_{13} = \frac{P_0}{2} [1 - \cos(\Delta)]$$

$$P_{14} = \frac{P_0}{2} [1 + \cos(\Delta)]$$

where $\Delta = \phi_1 - \phi_2$. The output of the interferometer is a periodic function of the phase shift and is shown in FIG. 1B. If the power on the two detectors is summed the total power is just the power from the laser $P_o$. The output of the interferometer is a periodic function of the phase shift. It is possible for the overall phase shift to be such that for small disturbances there is no change in the power onto the photoreceivers at all. Moreover, there will be low frequency disturbances that will cause large changes in the interferometer sensitivity. These low frequency disturbances will be controlled by using feedback.

II. Conversion of Optical Power into Electronic Signals

The optical power P is converted in the detection process into a current by the photodiode and the photocurrent i is related to the optical power by the current responsivity R.

$$i = RP$$

The photodiode current is converted into a voltage by a transimpedance amplifier with a feedback resistor $R_T$.

$$V = R_T i$$

The photodiode, transimpedance amplifier and voltage amplifier combination constitute the photoreceiver. The voltage after the photoreceiver gain stage with gain $G_{rec}$ is equal to $$V = G_{rec} R_T i$$

The two voltages from the two photoreceivers are amplified by a differential amplifier whose voltage output is equal to the difference between the two voltages input. The output from the differential amplifier is called the error signal and equals, $$V_{error} = G_{rec} R_T R[P_{14} - P_{13}] = G_{rec} R_T R P_0 \cos(\Delta)$$

This error signal is used to provide a feedback correcting signal to the interferometer PZT mirror 4 to correct the phase difference between the two arms of the interferometer in order to maintain the operating point of the interferometer at maximum sensitivity. The difference between the powers on the two photodetectors is plotted in FIG. 1B. This error signal has several excellent properties for feedback control. First the slope is very steep at the operating point. Second the slope is linear. Third the signal is signed, i.e., when the phase difference to be controlled is zero the error signal is zero and the error signal changes sign from positive to negative as it goes through zero.

The response of the interferometer to the small phase shifts produced by the bound protein is a function of the difference between the two paths through the interferometer. The phase shift where the signal from the photodetectors changes most rapidly with phase shift is $\pi/2$ and is called the operating point of the interferometer. At the operating point the derivative of the signal power with respect to the phase shift is a maximum. Because the interferometer is subject to environmental disturbances that can change the path lengths it is necessary to control the phase difference using active control. Moreover the disc 6 itself can produce disturbances that will move the interferometer away from the operating point. This results from the variations in thickness in the disc from point to point. These variations must be controlled by feedback if the interferometer is to remain at the operating point.

III. Feedback Control and Servo Amplifier

The error signal is amplified and bandwidth limited by a low noise, high gain servo amplifier with gain $G_{servo}(f)$ that is a function of frequency, f, and then further amplified to high voltage by the high voltage amplifier with gain $G_{HV}$. The output voltage of the high voltage amplifier is called the control signal and is equal to $$V_{control} = G_{HV}G_{servo}(f)G_{rec}R_TRP_0\cos(\Delta)$$

When the servo amplifier is on, the control voltage applied to the PZT will move the mirror until the error signal is zero. Thus, the operating point of the interferometer is such that $$\Delta = \pi/2$$

Disturbances from this operating point will be suppressed by the feedback loop. If we call the small disturbances to the phase difference δ, then the control voltage is $$V_{control} \approx G_{HV}G_{servo}(f)G_{rec}R_TRP_0\delta,$$

provided that the bandwidth of the servo is sufficient to compensate for any disturbances to the phase difference between the two arms which result in a nonzero error signal and which will lead to a control voltage that will drive the PZT to suppress the disturbance. Thus within the servo bandwidth, the control signal is a negative image of the disturbance inside the interferometer.

IV. Disc Configuration

Figure 2:
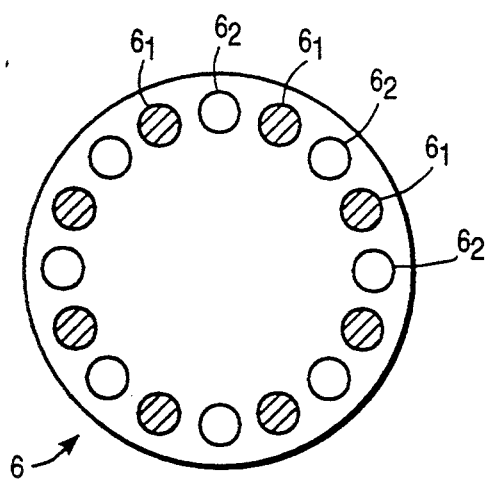
FIG. 2 is a plan view of one embodiment of a disposable sample disc employed in the system of the present invention.

FIG. 2 illustrates a sample disc 6 with circular spots of antibody. Disc 6 is preferably a plastic or glass disc on which is coated spots $6_1$ of antibody to antigen A and spots $6_2$ of antibody to antigen B. When the disc is incubated with antigen A there is binding between antibodies to A and antigen A but there is no binding between antibodies to B and antigen A.

In other words, disc 6 has spots $6_1$, $6_2$, of antibody which are alternately specific for antigen A and not specific for antigen A, respectively. These spots $6_1$, $6_2$ form a ring around the edge of the disc through which the signal and reference beams will travel. Before the disc is incubated with a sample of antigen A the phase shift experienced by a beam passing through the spots is the same for all spots. To test a sample for antigen A the sample must be incubated on the sample disc.

During incubation the antigen A binds only to the antibodies for A. Spots $6_1$ consisting of antibodies and bound antigen now produce a different phase shift than spots $6_2$ made up of antibodies that have not bound. Thus after incubation, as the disc spins the signal beam experiences a periodically varying phase shift with a frequency equal to the rotation frequency of the disc times the number of bound spots $6_1$ on the disc circumference. Similarly the reference beam, which passes through a spot adjacent to that traversed by the signal beam, also experiences a periodically varying phase shift. The signal and reference beam phase shifts are 180 degrees out of phase because when the signal beam is in a bound spot $6_1$ the reference beam is in an unbound spot $6_2$ and after the disc rotates by one spot the signal beam is in a new unbound spot $6_2$ and the reference beam is in the bound spot $6_1$ that the signal beam was just passing through.

As the disc spins at frequency, Ω, the optical path length through the disc changes as the light signal (reference) beam passes alternately through the bound (unbound) and the unbound (bound) regions which have different optical path lengths due to the additional material in the bound regions.

Next considered is the optical path length and phase shift. The difference in optical path lengths is computed. Spots $6_1$ with both antibody and antigen are called bound spots and those with only antibody unbound spots $6_2$. First the signal beam passes through a bound spot $6_1$ and the reference beam passes through an unbound spot $6_2$. Then, when the disc has rotated one spot the signal beam now passes through an unbound spot $6_2$ and the reference beam passes through a bound spot $6_1$. Thus the phase difference between the two beams is alternating at a frequency equal to the rotation frequency of the disc times the number of bound spots $6_1$. This phase difference is next computed.

Figure 3:
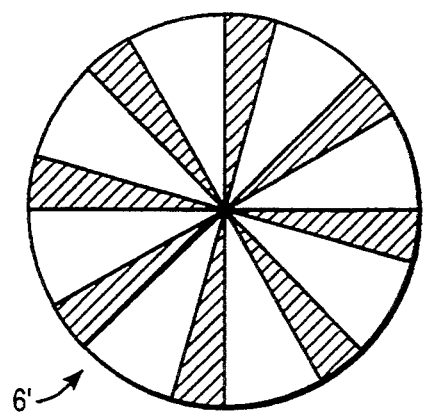
FIG. 3 is a plan view of another embodiment of a sample disc which can be employed in the system of the present invention.

In contrast to the disc 6 shown in FIG. 2, the disc of FIG. 3 can also be used. In FIG. 3, disc 6' is provided with wedge shaped active and inactive binding reagent regions as shown in FIG. 3 of above-identified U.S. Pat. No. 4,537,861, the teachings of which are incorporated by reference herein.

V. Optical Path Length

The optical path length, 0, is used to compute the accumulated phase shift rather than the physical distance because the wavelength is a function of the refractive index n at each point in space and so the phase accumulates at different rates along the optical path depending on the refractive index of the medium. Mathematically the optical path length along a path from a to b is the refractive index n(x) integrated over the path from a to b $$O = \int_a^b n(x)dx$$

The phase accumulated after an optical path length O is given by $$\phi = 2\pi \frac{O}{\lambda}$$

Thus the phase accumulates by $2\pi$ in an optical path length $O = \lambda$.

VI. Phase Shift

Next considered is the phase modulation at frequency $f_{sig}$, also called the signal frequency. If the rotation of the disc is Ω and the number of bound spots on the disc is N then $$f_{sig} = n\Omega$$

The phase variation 6 is determined from the difference between the optical path length through the bound protein and the unbound protein $$O_{bound} = \int_a^b n(x)dx = n_{glass}l_{glass} + n_{ab}l_{ab} + n_{ag}l_{ag}$$

$$O_{unbound} = \int_a^b n(x)dx = n_{glass}l_{glass} + n_{ab}l_{ab} + l_{ag}$$

In these equations the l's are the height of the proteins and the n's are the refractive index of the proteins (ab for antibody and ag for antigen). The changing phase shift is $$\delta = 2\pi \frac{O_{bound} - O_{unbound}}{\lambda} =$$

$$2\pi \frac{(n_{glass}l_{glass} + n_{ab}l_{ab} + n_{ag}l_{ag}) - (n_{glass}l_{glass} n_{ab}l_{ab} + l_{ag})}{\lambda}$$

After subtraction, $$\delta = 2\pi \frac{l_{ag}}{\lambda} (n_{ag} - 1)$$

Next considered is the refractive index of the protein layers. The refractive index of the protein layers is modeled using the Maxwell Garnet formula. This model assumes that the refractive index of a several component layer is the volume weighted average of the refractive indices of the components making up the layer. It is assumed that a fully packed protein layer has a refractive index of $n^{full}_{ag} = 1.3$ and air has a refractive index of $n_{air} = 1.0$. The formulae for the refractive index is then just $$n_{ag} = \frac{n_{air}V_{air} + n^{full}_{ag}V_{ag}}{V_{Tot}}$$

For low concentrations the volume of protein is small and in a unit area on the disc the formulae becomes approximately $$n_{ag} \approx 1 + n^{full}_{ag} \frac{V_{ag}}{V_{Tot}}$$

Now if the individual proteins have height 1, base area $w^2$ and surface concentration $\rho$, then the volume of all of the protein covering a unit area, A, on the disc 6 is $$V_{ag}Aw^2l\rho$$

The total volume that could be occupied is $$V_{tot} = Al$$

Substituting in for the two volumes, $$n_{ag} \approx 1 + n_{ag}^{full}W^2\rho$$

VII. Feedback

Next considered are feedback schemes that can be used for the control of one of the mirrors to keep the interferometer at the operating point, i.e., on the steep linear part of the fringe. These feedback arrangements include: a) narrowband, b) broadband and c) split feedback.

a. Narrowband servo excludes the signal

If the servo bandwidth is less than the signal frequency $f_{sig}$ then the disturbances in phase produced by the antigen will not be seen by the servo amplifier and so they cannot be suppressed. Thus the photodetector output will contain a signal that is proportional to the amount of antigen on the disc but the control signal will not. The control signal will contain information on the environmental disturbances to the interferometer, for example temperature changes and vibrations, and variations in the thickness of the disc 6 between the two points of impingement of the signal and the reference beams. The temperature variations will be at very low frequency provided the interferometer is thermally insulated from the environment and the thermal mass of the interferometer is large. The vibrations can be attenuated by a simple seismic isolation stack consisting of alternating layers of lead and rubber which support the interferometer. The absolute variations in the disc thickness are not important. What is important is only the difference in the thicknesses between the positions of the reference and the signal beams, which is what changes the phase. The distance between the two beams is kept to a few millimeters or less, so provided that the disc thickness does not change rapidly over this small distance the phase disturbances will be small and at low frequency. The frequency at which these disturbances occur will be near the rotation frequency of the disc and not the much higher frequency of the signal.

With a narrowband servo, the servo amplifier filters out the high frequency signal and provides a low bandwidth error signal that contains all of the large phase shift low frequency disturbances that would move the interferometer away from the operating point. The signal is then taken at a point A between the differential amplifier and the servo amplifier. This high frequency signal can then be amplified up with a narrow band low noise ac amplifier and then measured using phase sensitive detection as described below.

b. Broadband servo includes the signal

If the servo bandwidth is greater than the signal frequency $f_{sig}$ then the disturbances in phase produced by the antigen will be seen by the servo amplifier and they will be suppressed. Thus the photodetector output will not contain a signal that is proportional to the amount of antigen on the disposable disc, but the control voltage at point B in FIG. 1A will contain a signal at frequency $f_{sig}$ which is proportional to the amount of antigen bound. In this case, the signal is taken at point B.

c. Split feedback schemes

If the PZT displacement actuator does not have sufficient range of motion, because the low frequency disturbances are too great, then a second actuator can be placed in the interferometer. This second actuator will have large range of motion but low bandwidth. Thus the error signal will be split into two error signals. One error signal will have the high frequency information and will be fed back to the high frequency actuator and the other error signal will have low frequency information and will be fed back to the low frequency actuator. In this way both broad bandwidth and large displacement are obtained.

VIII. Combined Beamsplitter/Mirror

Figure 8:
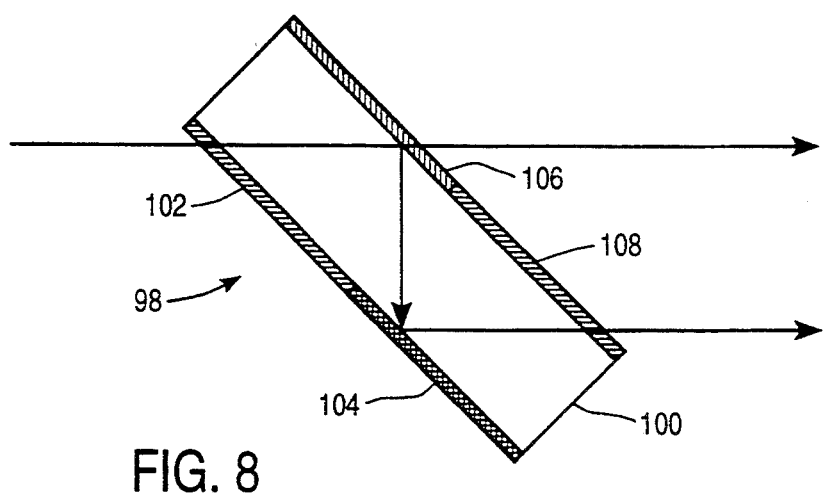
FIG. 8 is a side view of a Combined beamsplitter mirror element which can be used in the embodiment of FIG. 1.

To save space and make the interferometer less sensitive to vibration, a beamsplitter and mirror can be combined into one by means of a single element 98 as shown in FIG. 8. In FIG. 8, a beamsplitter-mirror combination is produced by providing a glass substrate 100 having an anti-reflection coating 102 and a high reflection coating 104 provided on one side and a partially reflecting coating 106 serving as a 50/50 beamsplitter and an anti-reflection coating 108 provided on the opposite surface of glass substrate 100. In this way, the beamsplitter and mirror are combined on a single optical element. The anti-reflection, high reflection and 50/50 splitter coatings are all designed for 45° incident angle. When using the beamsplitter mirror element shown in FIG. 8, an incident light beam incident on anti-reflection coating 102 at an angle of 45° is partially transmitted by the coating 106 and partially reflected by coating 106 to high reflection coating 104, where the partially reflected beam is fully reflected by the coating 104 through anti-reflection coating 108. Thus, a beam incident at a 45° angle on coating 102 shown in FIG. 8 passes through coating 102, is split into two equal power beams by coating 106, one of which passes through the coating 106 and one of which is reflected down to high reflection coating 104 where it is reflected to and through anti-reflection coating 108.

Figure 9:
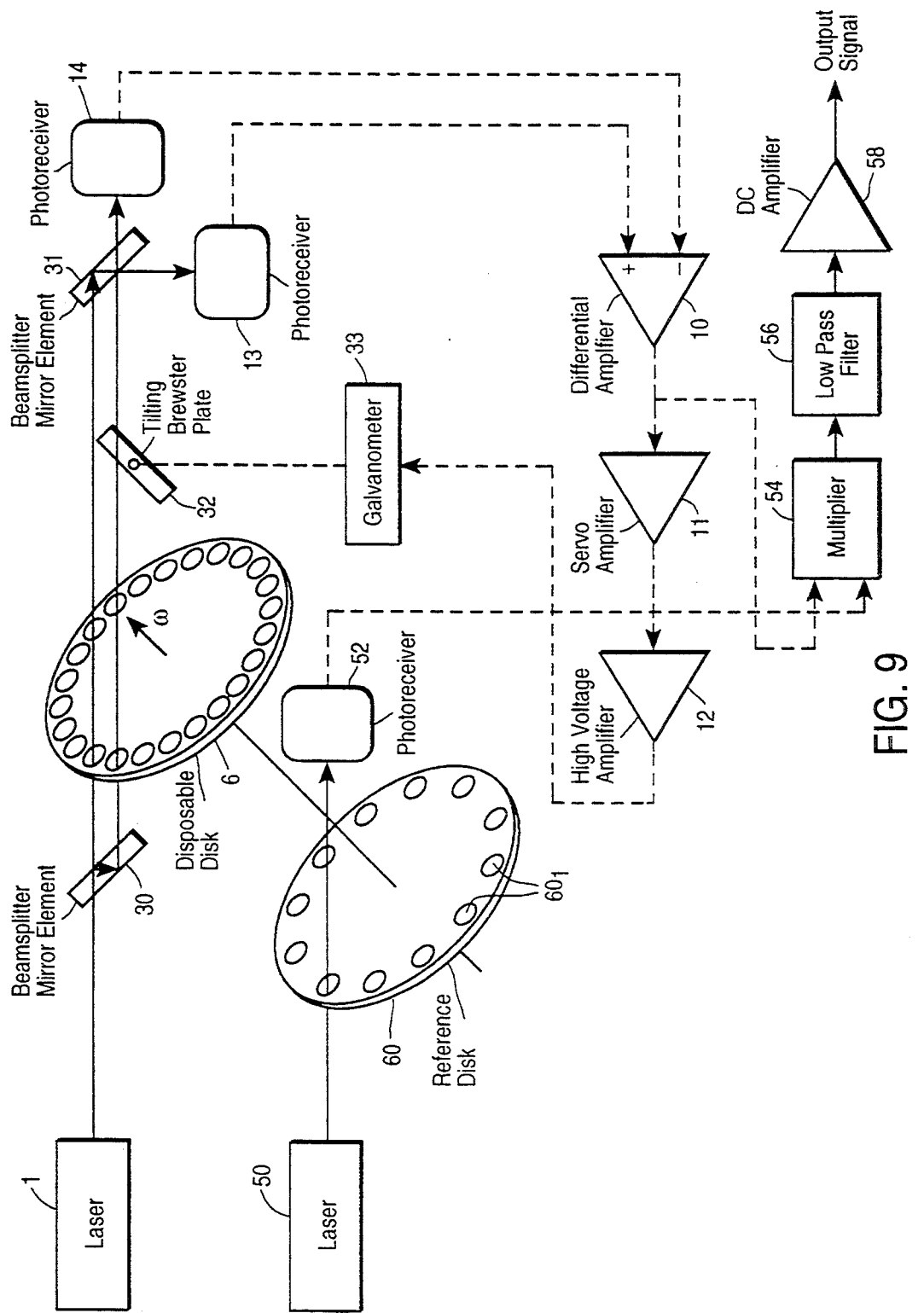
FIG. 9 is a schematic block diagram of an embodiment of the present invention utilizing a Mach Zehnder interferometer and the element of FIG. 8.

FIG. 9 illustrates an implementation of a Mach-Zehnder interferometer where the beamsplitters and mirrors are implemented as a pair of elements 30 and 31, each constructed in the manner of the combined beamsplitter-mirror element of FIG. 8. In this embodiment, because each of elements 30 and 31 fixes in place the mirror and beamsplitter, it is not possible to use PZT 7 to produce the desired phase difference between the signal and reference laser beams. In FIG. 9, this is instead accomplished using a Brewster plate 32, which can be rotated by a small angle using a galvanometer 33 to change the optical path length of one of the signal and reference beams. Alternatively, an electro-optic element could be interposed in the path of one of the beams.

IX. Signal Processing

The embodiment of FIG. 9 also includes phase sensitive detection, next discussed.

a. Phase Sensitive Detection

Unlike many detection problems, the phase and frequency of signal in the present invention are known. Thus if a second metal disc 60 as shown in FIG. 9 is attached to the same motor shaft as disc 6 and if in addition this second disc 60 has holes $60_1$ corresponding to the positions of the bound antigen spots, these $60_1$ holes can be used to produce a strong electronic reference signal at the sample signal frequency by means of a laser 50 and a photoreceiver 52. The error signal from the interferometer, i.e., the output of the differential amplifier 10 in a narrowband servo, is at a frequency which is well above the 1/f noise of the amplifiers and so it can be amplified at low noise. If the amplified error signal is then multiplied by multiplier 54 with the electronic reference signal the output of the multiplier will have a component at the twice the signal frequency and one at the difference frequency or DC. This DC signal can then be low pass filtered by filter 56 and then applied to a DC amplifier 58. The signal has the low noise resulting from low noise AC amplification and the narrow noise bandwidth resulting from the low pass filter. In this way, it is possible to employ a lock-in amplifier as taught by Willison, Lasers & Applications, pp. 73–76, March 1983.

b. Digital Signal Processing

A more flexible and general way to average the data is to store all of the signal measurements and reference measurements in a computer and perform the averaging digitally. This has several advantages over the analog technique. No information is lost by doing the signal processing in this fashion. If the data is recorded digitally each measurement is tagged with information on where the measurement was made on the substrate and the reference signal information is also recorded so that it is then possible to process the data in many different ways. For example, 1) the data could be analyzed exactly like the analog lockin by multiplying the signal by the reference and then low pass filtering, 2) the signal data could be sifted for a signal that looks like the reference signal, 3) the data could be high pass filtered and then cut into N strings of data that exactly correspond to one period of the reference signal and then these strings of data can be averaged point by point, 4) all of the locations on the substrate could be measured several times and then the data at each of these locations could be averaged before the data is further averaged or filtered, 5) by recording all of the measurements before signal processing it becomes possible to perform a statistical analysis of the individual locations on the substrate to look for bad data caused by imperfections in the substrate or contamination, 6) measurements can be made before incubation and after incubation to look for the buildup of signal corresponding to protein, 7) by digitally recording the data it also becomes possible to analyze the data several different ways and compare the results, and 8) the measurement locations can be in any pattern on the substrate as long as the computer knows when it is looking at analyte and when it is not.

X. Sensitivity Calculations

Next computed is the sensitivity of the technique if the source of noise is photon shot noise, for a Mach-Zehnder interferometer.

a. Shot Noise:

To determine the sensitivity, an estimate for the detection noise is needed. Shot noise is assumed for this calculation, which for light of frequency $v$ and power $P_o$, in a bandwidth B is just $$i_{noise} = \sqrt{P_o h v B R^2}$$

Minimum Detectable antigen surface concentration:

The minimum measurable signal occurs when the signal equals the noise, $$\frac{S}{N} = \frac{i_{signal}}{i_{noise}} = \frac{\pi n_{ag}^{full} \frac{l_{ag}}{\lambda} w^2 \rho P_0 R}{\sqrt{P_0 h v B R^2}} = 1$$

Substituting in for the signal and solving for the minimum surface concentration, $$\rho_{min} = \frac{\sqrt{P_o h v B}}{\frac{l_{ag}}{\lambda} w^2 P_0} = \frac{\sqrt{hv}}{\pi n_{ag}^{full}} \sqrt{\frac{B}{P_0}} \frac{\lambda}{l_{ag}} \frac{1}{w^2}$$

b. Minimum Detectable Surface Concentration

To determine the sensitivity or detection limit begin by substituting into the equation for the minimum detectable surface concentration the following values.

$$hv = \frac{hc}{\lambda} = \frac{6.6 \times 10^{-34} [Js] \, 3 \times 10^8 [m/s]}{6.33 \times 10^{-7} [m]} = 3.1 \times 10^{-19}$$

$n_{ag}full \gtrsim 1.3$ $P_o = 10^{-3} [W]$ $\lambda = 6.33 \times 10^{-7} [m]$ $l_{ag} = 10^{-9} [m]$ $w^2 = 10^{-18} [m^2]$ $B = 1 [Hz]$ From these numbers is obtained a minimum detectable surface concentration of $$\rho_{min} = \frac{\sqrt{h\nu}}{\pi n_{ag}^{full}} \sqrt{\frac{B}{P_0}} \frac{\lambda}{l_{ag}} \frac{1}{w^2} =$$

$$3.7 \times 10^{11} \left[\frac{1}{m^2}\right] = 3.7 \times 10^5 \left[\frac{1}{mm^2}\right].$$

In dimensionless form this equation becomes $$\rho_{min} = \frac{\sqrt{hc}}{\pi n_{ag}^{full}} \sqrt{\frac{B}{1\,Hz}} \sqrt{\frac{633\,nm}{\lambda}} \sqrt{\frac{1\,mW}{P_0}} \left[\frac{10A}{l_{ag}}\right]\left[\frac{10A}{w}\right]^2 =$$

$$3.7 \times 10^5 \sqrt{\frac{B}{1\,Hz}} \sqrt{\frac{633\,mn}{\lambda}} \sqrt{\frac{1\,mW}{P_0}} \left[\frac{10A}{l_{ag}}\right]\left[\frac{10A}{w}\right]^2$$

c. Minimum Detectable Solution Concentration

If the total spot area is 1 mm² and these molecules have a molecular weight of 1000 gm and are in a 0.1 μl sample the solution concentration is $$\text{Mass} = 1000 \frac{3.7 \times 10^5}{6.6 \times 10^{23}} = 5.6 \times 10^{-16} [gm]$$

$$\text{Concentration} = \frac{\text{Mass}}{\text{Volume}} =$$

$$\frac{5.6 \times 10^{-16} [gm]}{0.1\,\mu l} = 5.6 \times 10^{-12} \left[\frac{gm}{ml}\right] = 5.6 \left[\frac{pg}{ml}\right]$$

XI. Practical Detection Problems a. Disc Wobble

Figure 4:
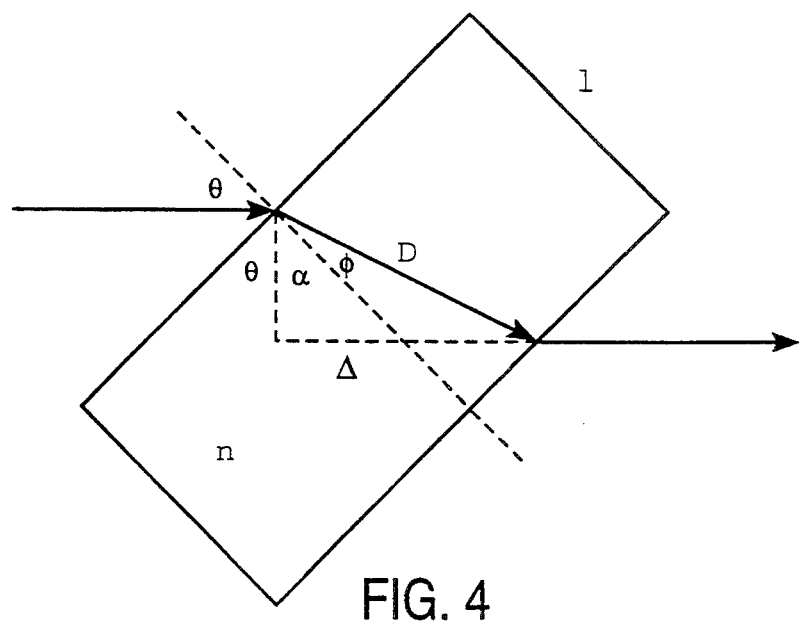
FIG. 4 is an optics diagram illustrating the optical geometry of a laser beam passing through the sample disc of the present invention.

The disc will have a tendency to wobble at the frequency of rotation and this will produce an apparent signal at the rotation frequency. This will be below the real signal frequency by a factor equal to the number of spots or wedges on the disc. The disc is inserted at an angle $\theta$, as shown in FIG. 4, and the angle of propagation inside the disc is equal to $\phi$ and the angle of propagation inside the disc is equal to which is given by Snell's law.

$$\sin(\theta) = n\sin(\phi)$$

Solving for the angle $\phi$ we find $$\phi = \arcsin\left[\frac{\sin\theta}{n}\right]$$

Thus the optical path length in the disc when the disc is in at angle $\theta$ is $$O = nD = n\frac{1}{\cos(\phi)}$$

But the optical path outside of the disc also changes because as the disc incident angle changes the exit point on the disc moves. The optical path outside of the disc becomes $$O_{air} = l - \Delta = l - D\sin\left[\left(\frac{\pi}{2} - \theta\right) - \phi\right] =$$

$$l - \frac{l}{\cos(\phi)} \sin\left[\left(\frac{\pi}{2} - \theta\right) - \phi\right]$$

which can be rewritten as $$O_{total} = O_{disc} + O_{air} =$$

$$l\left\{1 - \frac{n}{\cos(\phi)} - \cos(\theta) - \tan(\phi)\sin(\theta)\right\}$$

Substituting in from Snell's law and expanding to second order, $$O_{total} \cong l\left(n + \frac{\theta^2}{2}\right)$$

For small angular displacements of the disc the optical path length changes by $$\partial O_{total} \cong l\theta\partial\theta$$

So if the disc is 1 mm thick within 1 degree of normal and the excursions are less than 1 degree, the optical path changes by 0.3 μm, which is less than ½ wavelength for helium neon. This is easily within the dynamic range and bandwidth of the servo.

b. Disc Nonuniformity

Refractive index variations, surface roughness and nonuniform thickness will product random fluctuations in the phase difference between the two beams. This is a noise source and could in addition move the interferometer away from its optimum operating point. To reduce this problem the signal and reference beams should be as close together on the disc 6 as possible because the thickness changes in the disc 6 will occur over a distance large compared to the spot separation. The phase disturbances due to the disc will be at a lower frequency than those due to the spots because the disc thickness for small separations is highly correlated. These disc variations will lead to disturbances in the phase at frequencies within the bandwidth of the servo and so they will be suppressed. Because they are at a lower frequency than the signal they can then be filtered out electronically using phase sensitive detection. In addition, if the signal and reference beams are close together the disc thicknesses at these two points will be highly correlated and so the disturbances will be small. The disc nonuniformities that occur at the spatial frequency of the spots will appear as noise that cannot be suppressed by the servo because they are beyond the servo bandwidth. But these disturbances are also not in phase with the reference disc and so will be averaged out by the phase sensitive detection.

c. Disc Wedge

If the disc is wedged there is a change in the disc thickness of Δl over the diameter of the disc d. For a distance between the laser beams a on a disc having a refractive index n, a phase excursion of $\phi$ is observed:

$$\phi = 2\pi n \frac{\Delta l a}{d\lambda}$$

For a 1 cm diameter disc 6 with refractive index 1.46 with laser spots 1 mm apart and with a wedge of 1 mrad at 633 nm the phase excursion is 0.6 mrad. This small disturbance is within the servo bandwidth because it occurs at the rotation frequency of the disc.

One source of noise in the measurements results from variations in the amount of antibody and antigen bound to the substrate in preparation for the incubation of corresponding antigen or antibody. There are two sources of noise. First, to the extent that the surface concentration varies the signal will vary from spot to spot. Second, in addition the amount of bound analyte will also vary because the amount of it bound to the surface will vary with the surface concentration of antibody or antigen bound to the surface in preparation for analyte measurement in the first place. The signal will vary from measurement location to measurement location on the substrate. This variation can be reduced by averaging over many independent measurement locations on the substrate.

d. Disc Thickness Variations

Figure 5:
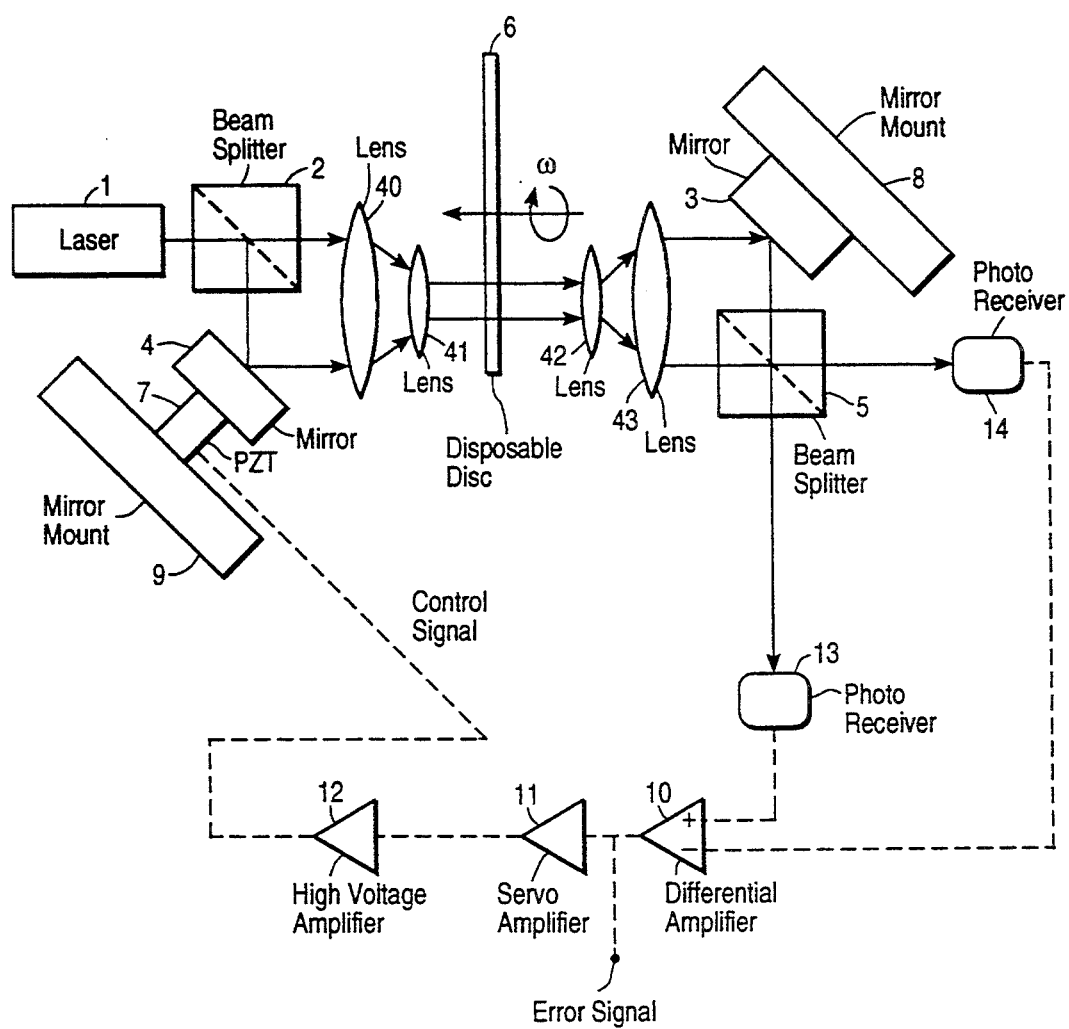
FIG. 5 is a block diagram of a modified version of the embodiment shown in FIG. 1.

One source of noise in the measurements results from variations in the substrate thickness from place to place on the substrate. While the absolute thickness of the substrate does not matter and the difference in the substrate thickness between the two beam positions does not matter the change in this difference from place to place on the disc is a source of noise. This can be reduced in several ways. First, the two beam positions on the substrate can be made as close together as possible so that the thicknesses variations are as highly correlated as possible. As shown in FIG. 5 the positions of the beams, while maintaining beam colinearity, can be made very close by placing a pair of lenses 40, 41 before the substrate and a similar pair 42, 43 after the substrate. These lens pairs 40, 41 and 42, 43 will bring the light paths close together for passage through the substrate and then move them apart for recombining with the second mirror and beamsplitter. In addition the light beams will be reduced in size so that they can examine smaller regions on the substrate and so allow as many spots as possible on the substrate.

A second way to reduce the noise due to the disc thickness variations is to make measurements at as many different positions on the substrate as possible. Measuring at the same positions on the substrate over and over again will reduce the random noise but the same substrate thickness variations will be measured repeatedly and these will not be averaged. The full power of the lockin detection requires that the measurements be independent. The signal processing can then be done either using the lockin measurements in real time or by digital data processing after the accumulation of signal and reference in the computer.

Figure 6:
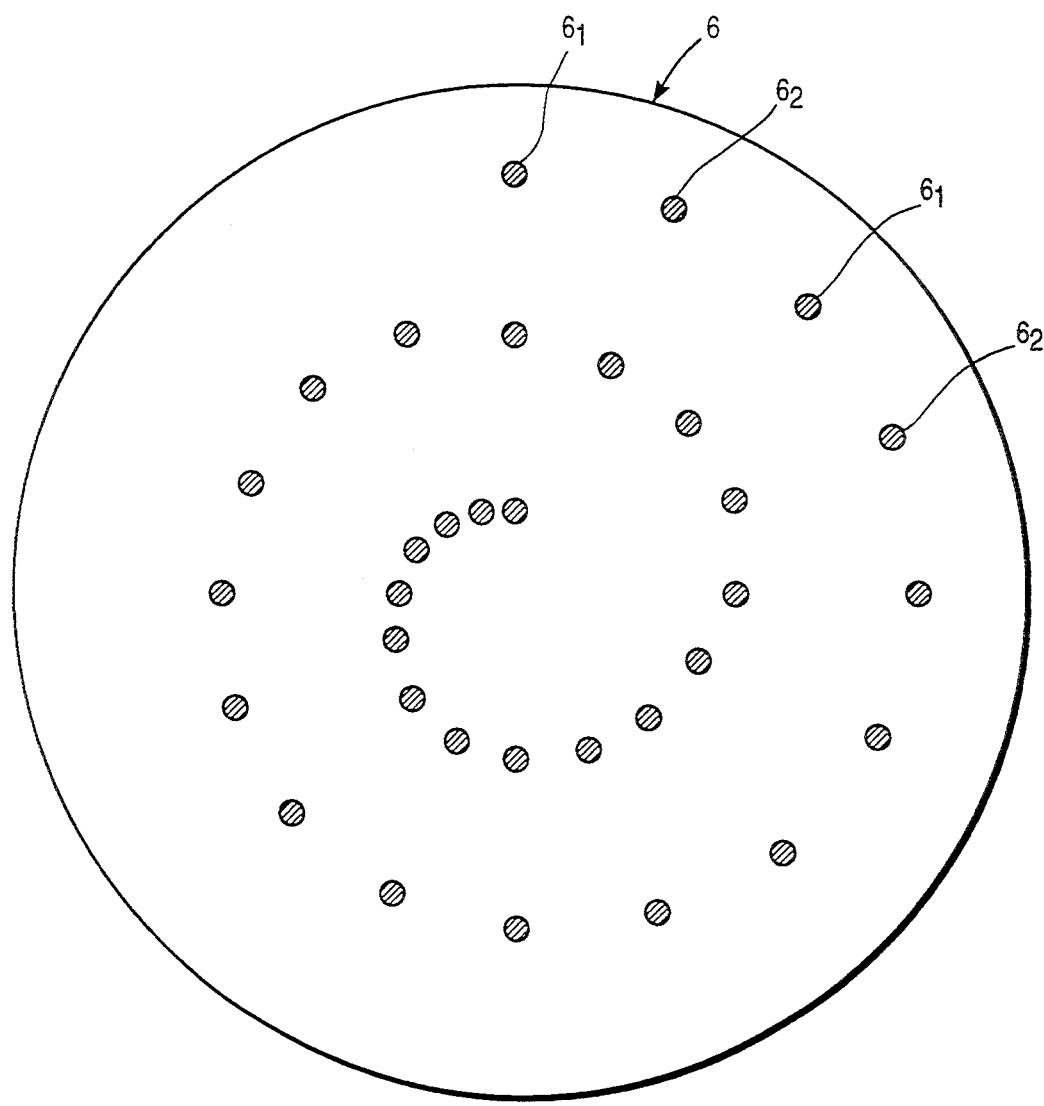
FIG. 6 is a plan view of another embodiment of a disposable sample disc which can be used according to the invention.

A good arrangement for these type of measurements on a disc, for example, would be to have the measurement spots arranged in a spiral pattern as shown in FIG. 6. As the disc spins the measurements are made with the interferometer along the spiral from spot 1 to spot 2 and so on. As the disc spins the measurement points on the substrate will have to be moved toward the center of the disc.. This can be done by translating the disc center of rotation or translating the interferometer with respect to the disc center of rotation. If the spots on the disc are small it may be necessary to track the measurement position on the disc by imprinting a set of guiding marks on the disc to indicate the position of a given measurement. These marks could be a set of depressions or bumps imprinted on the disc of known depth at a fixed distance from the protein spot positions. In this way the light beam positions on the substrate could be known at all times. This type of tracking would be much like that of a compact disc player. However, since the protein spots on the disc will be much larger than the bits on a compact disc it should be much easier.

In addition, this arrangement of spots on the substrate makes it particularly easy to have more than one type of analyte receptor regions on the substrate and to program the instrument to follow a given set of spots for a particular test.

An easier arrangement still would be to have wedge shaped analyte receptor regions and then the reference signal would just have to encode the information on the angular position and no tracking would be required provided the beams were slowly moved toward the center of the disc as the disc rotates. This scheme has the additional advantage that it is easy to maintain a 50% duty factor between active and inactive receptor regions as the radial position of the beams changes.

XII. Other Interferometers

The Mach-Zehnder interferometer is not the only interferometer that can be used in an immunosensor. A Michelson interferometer can be modified so that the reference beam is reflected to an auxiliary mirror, where it is sent through the disc and then reflected back for combination with the signal beam for detection with a photoreceiver. To name but a few of the many other types of interferometers that may be used we list: 1) Jamin, 2) Fizeau, 3) Sirks-Pringsheim, and 4) Nomarski. Of these the Nomarski is particularly interesting because it is used in reflection, can be very small and has the two beam positions very close together. Because the Nomarski interferometer is so small it is easy to conceive of an interferometer that is used like a compact disc reading head and scans the surface of the substrate to make its readings.

Figure 7:
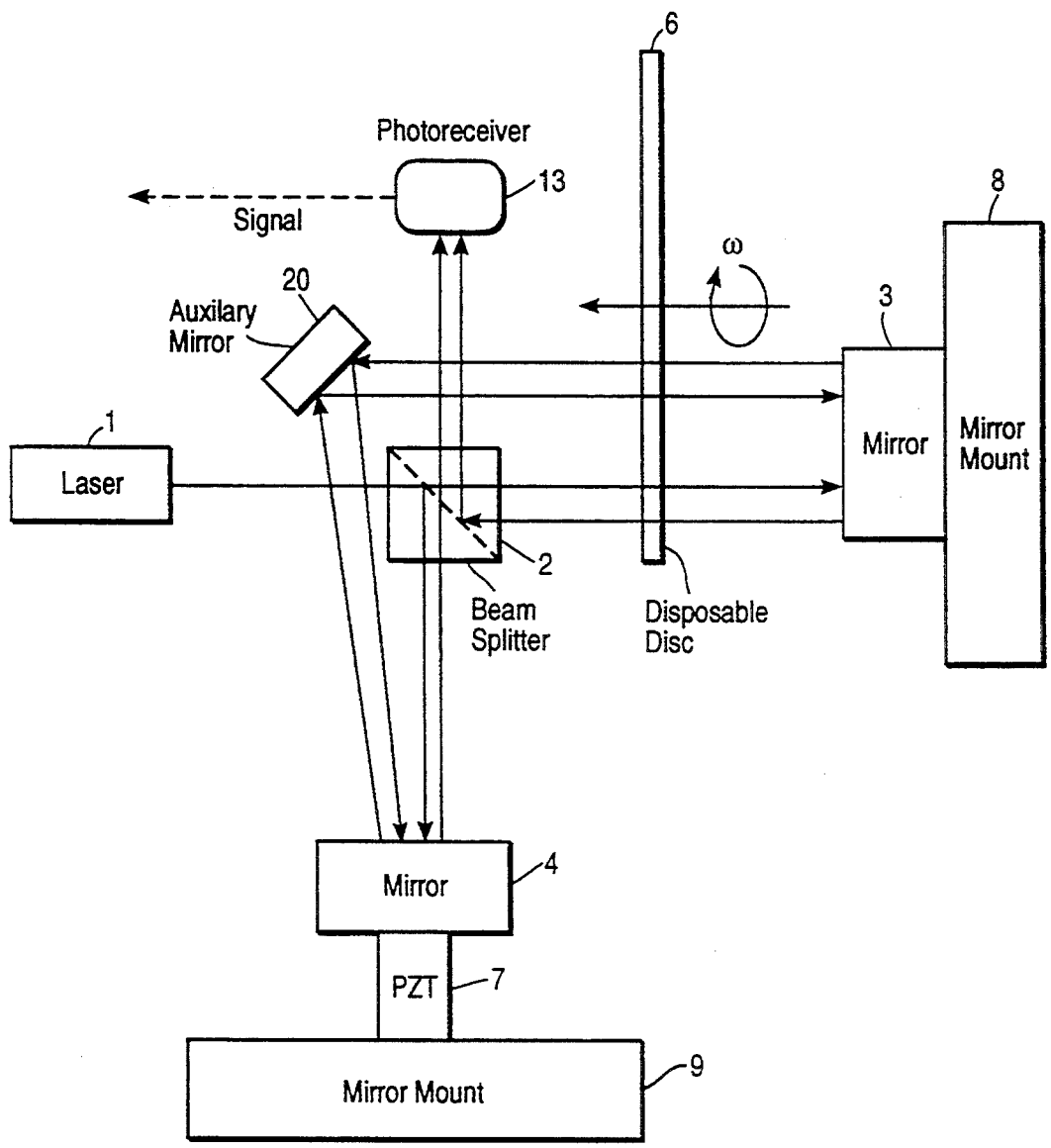
FIG. 7 is a schematic block diagram of a second embodiment of the present invention, employing a Michelson interferometer.

FIG. 7 is a schematic block diagram of such an embodiment employing a modified Michelson interferometer. In the embodiment shown in FIG. 7, the reference beam reflected from the mirror 4 is sent to an auxiliary mirror 20 where it is reflected through disc 6 and then reflected by the mirror 3 back toward the auxiliary mirror 20 through the disposable disc 6. Auxiliary mirror 20 then reflects the reference signal back to the mirror 4, where it is again reflected through the beamsplitter 2 and recombined with the signal beam.

In the modified Michelson interferometer of FIG. 7, the reference and signal beams pass through disc 6 so that the technique is less sensitive to the substrate thickness variations. Also, since the PZT mirror 4 is reflected from twice, therefore the reference arm path length changes twice as much for a given voltage to the PZT.

XIII. DC Measurements With CCD Arrays

Figure 10:
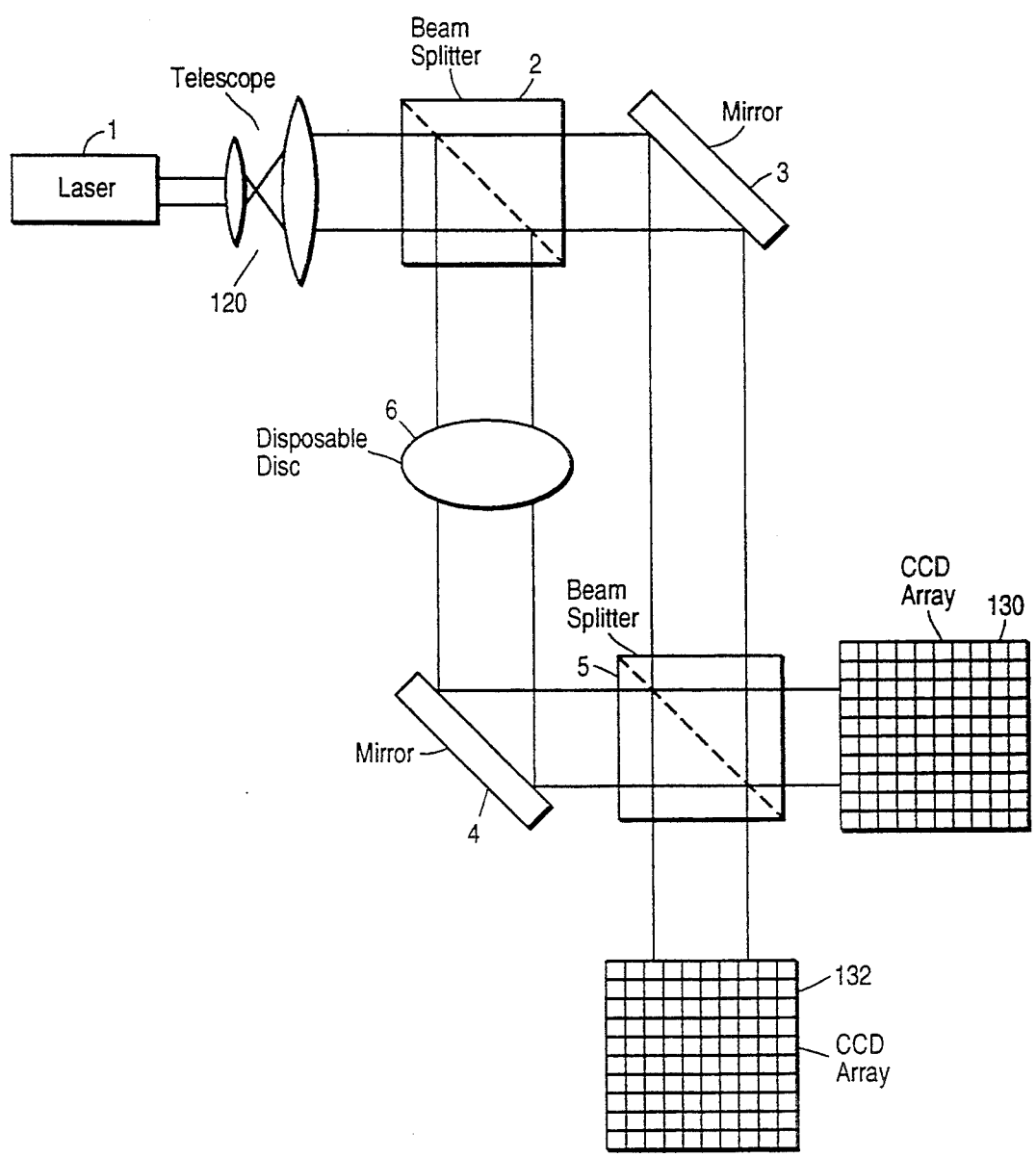
FIG. 10 is a schematic block diagram of an embodiment in which the sample disc remains stationary during the time that measurements are made.

In the event that random noise is less of a problem than the variation in the disc it may be possible to use an essentially DC technique. FIG. 10 shows such an arrangement. The laser beam is expanded in area by a telescope 120 and is used to interrogate many spots on the disc at once.

CCD arrays 130 and 132 are used to record the phase differences as a function of position on the disc. To cancel the nonuniformity of the CCD the disc (or substrate) is rotated into several positions and phase maps recorded. The disc may have several pedestals on the surface of known height so that the positions on the disc are known. In addition, the disc can be read both before and after incubation. In this way, it is possible to generate and store data on the underlying thickness variation of the disc. The predetermined pedestals can be used as control points to allow the operating point of the interferometer to be maintained.

XIV. Interferometer Beam and Disc Geometries

FIGS. 11A-11H show schematically various combinations of disc and beam configuration possible according to the present invention. Each figure shows the disc in a given orientation and the disc after it has rotated by 45 degrees. The open circles represent analyte bound to active binding agent and the stippled circles are inactive binding agent. The numbered X's represent the first and second (signal and reference) beams.

Figure 11A:
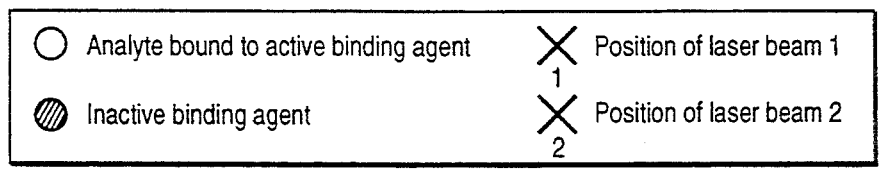
FIGS. 11A–11H are schematic representations showing different arrangements of active and inactive binding regions on the disc and beam positions relative to the disc.
Figure 11A:
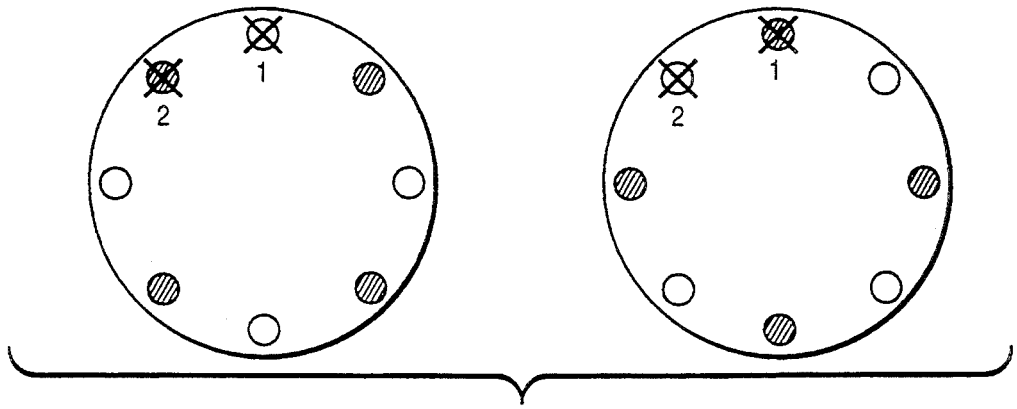

FIG. 11A shows a configuration where beam 1 passes through the bound analyte while beam 2 passes through the inactive binding agent. After the disc has rotated by 45 degrees, beam 1 passes through the inactive binding agent while beam 2 passes through the bound analyte.

Figure 11B:
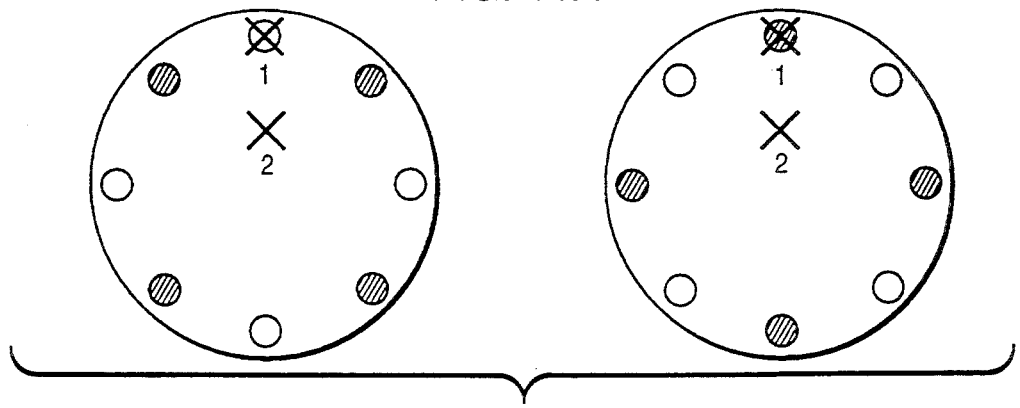

FIG. 11B shows a configuration where beam 1 passes through the bound analyte while beam 2 passes through an uncoated portion of the disc. After the disc has rotated by 45 degrees, beam 1 passes through the inactive binding agent while beam 2 passes through an uncoated portion of the disc.

Figure 11C:
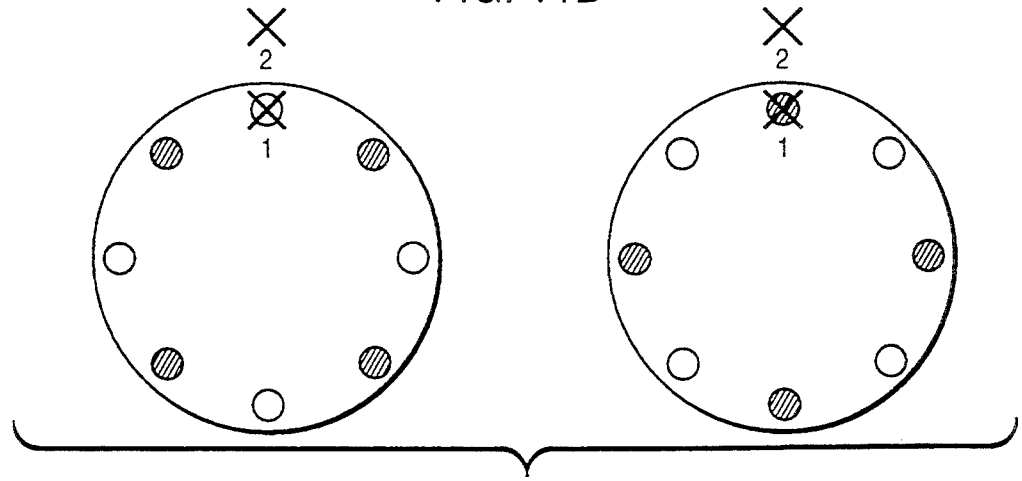

FIG. 11C shows a configuration where beam 1 passes through the bound analyte and beam 2 does not pass through the disc. After the disc has rotated by 45 degrees, beam 1 passes through the inactive binding agent and beam 2 does not pass through the disc.

Figure 11D:
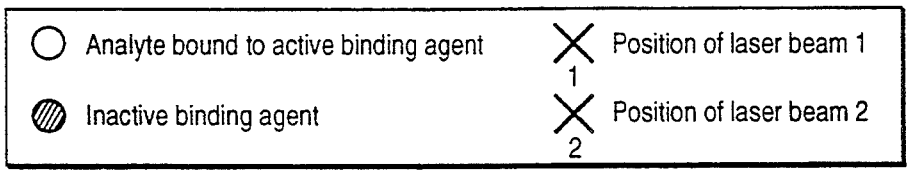
Figure 11D:
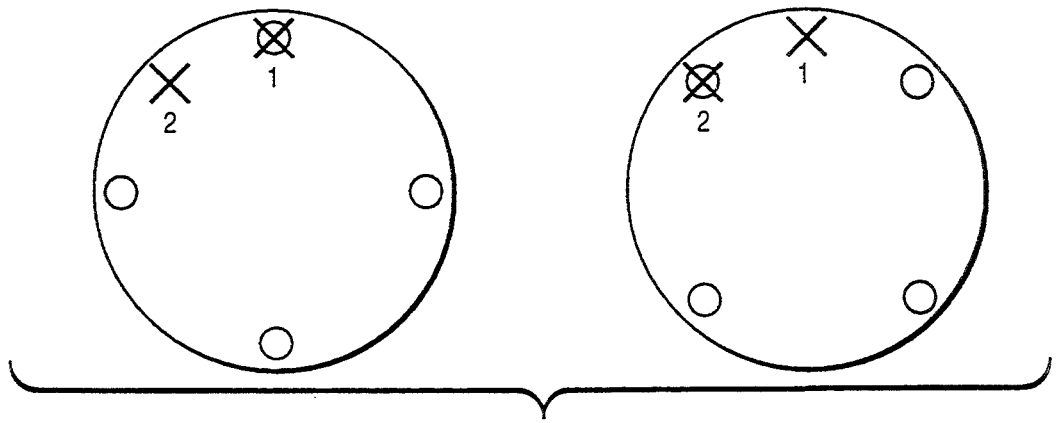

FIG. 11D shows a configuration where beam 1 passes through the bound analyte while beam 2 passes through an uncoated portion of the disc. After the disc has rotated by 45 degrees, beam 1 passes through an uncoated portion of the disc while beam 2 passes through the bound analyte.

Figure 11E:
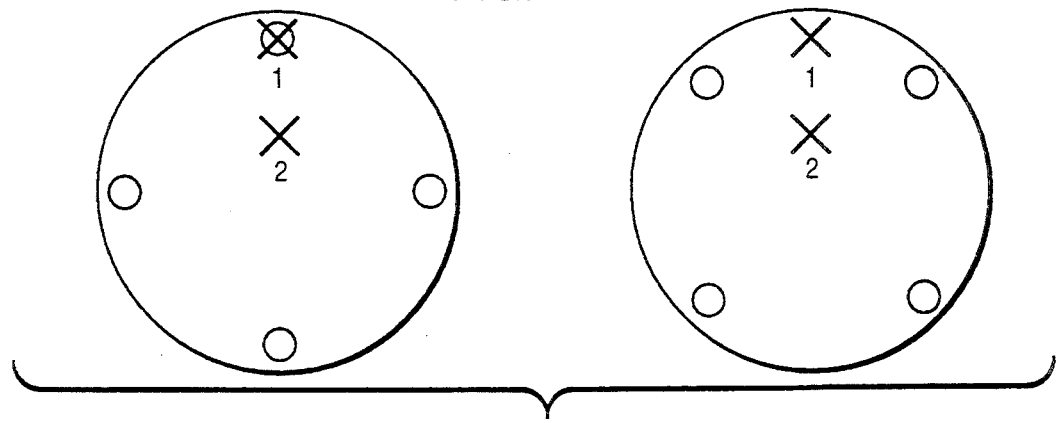

FIG. 11E shows a configuration where beam 1 passes through the bound analyte while beam 2 passes through an uncoated portion of the disc. After the disc has rotated by 45 degrees, beam 1 passes through the bound analyte while beam 2 passes through an uncoated portion of the disc.

Figure 11F:
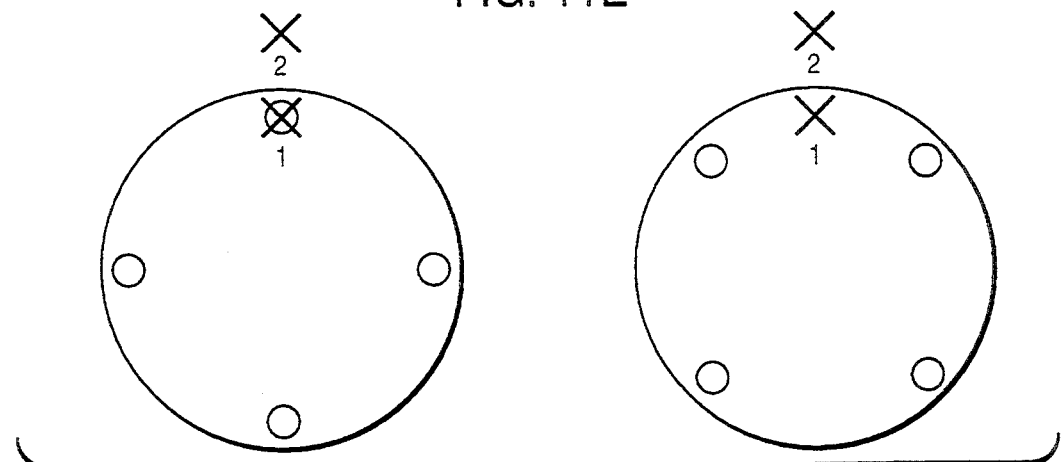

FIG. 11F shows a configuration where beam 1 passes through the bound analyte while beam 2 does not pass through the disc. After the disc has rotated by 45 degrees, beam 1 passes through the disc while beam 2 does not pass through the disc.

Figure 11G:
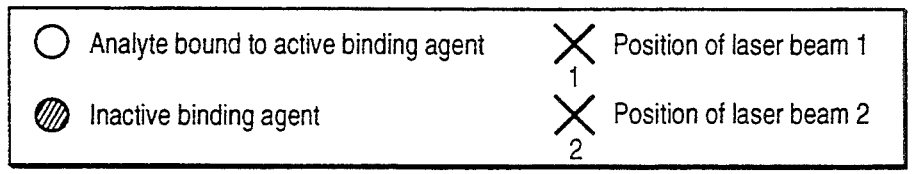
Figure 11G:
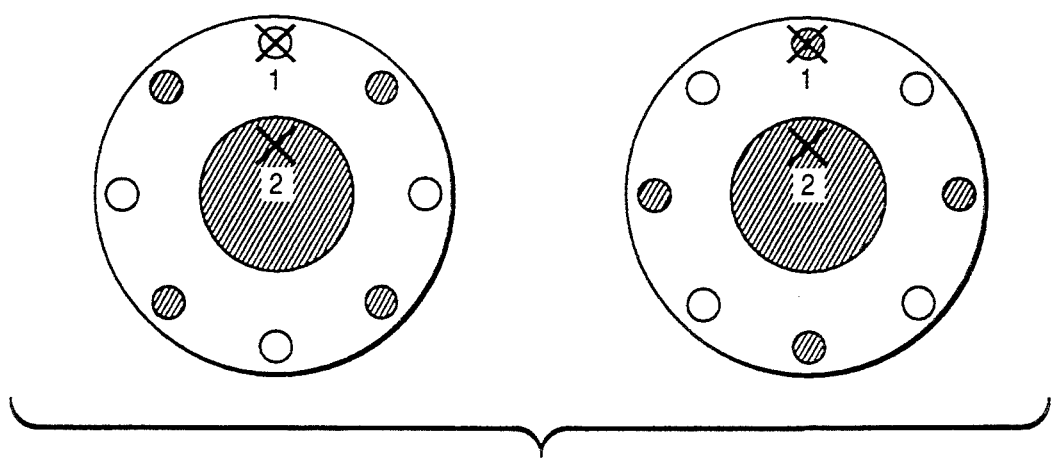

FIG. 11G shows a configuration where beam 1 passes through the bound analyte while beam 2 passes through the inactive binding agent. After the disc has rotated by 45 degrees, beam 1 passes through the inactive binding agent while beam 2 passes through the inactive binding agent.

Figure 11H:
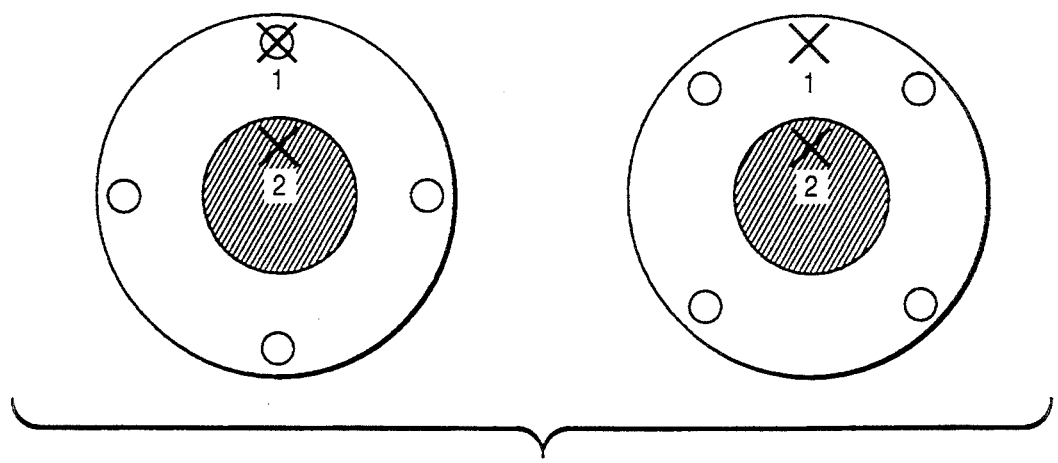

FIG. 11H shows a configuration where beam 1 passes through the bound analyte while beam 2 passes through the inactive binding agent. After the disc has rotated by 45 degrees, beam 1 passes through an uncoated portion of the disc while beam 2 passes through the inactive binding agent.

XV. Application of Binding Agent to Disc

The disc can be made of glass, plastic, or any other material having appropriate optical properties compatible with the interferometer. One member of the binding pair can be attached to the surface of the disc through passive adsorption, ionic interaction, covalent binding, or the like. Methods of attachment are well known to those skilled in the art and need not be further discussed.

The invention may be configured to help compensate for nonspecific binding. Nonspecific binding is binding which may result in an increase in the optical path length yet is not due to binding of the specific analyte of interest. One method of compensating for nonspecific binding is by attaching, to an area of the disc distinct from the active analyte receptor region, a molecule similar in chemical composition to the member of the binding pair to create a "non-specific binding region". If the active analyte receptor region is measured relative to this non-specific binding region, the difference in optical path will be due to the specific binding of the analyte in question.

For example, if the member of the binding pair attached to the active analyte receptor region is a monoclonal antibody specific for the analyte of interest, then a slight variant of this antibody that does not specifically bind the analyte of interest (nor specifically bind any other analyte found in the medium the test is carried out in), would be attached to the disk at a separate site defined as the non-specific binding region. Both regions on the disc would equally and non-specifically bind materials (other than the analyte) from the sample, e.g., non-specific protein binding, where the specific region would additionally bind the analyte of interest. The difference in optical path would thus result solely from binding of the analyte of interest.

Another method for making the areas of active and inactive binding agents on a surface comprises a first step of uniformly adhering a binding agent to the disc surface. This followed by a step of selectively deactivating selected areas of the binding agent to yield areas of active and deactivated binding agent by exposing the areas selected for deactivation to a deactivating amount of chemical or UV light.

The binding reagent applied to the disc is selected to bind with the analyte to be determined in the assay. It can be any member of the binding pairs described above. For example, it can be an antibody; antibody fragment selected from the group consisting of Fab, Fab' or F(ab')$_2$ fragments; hybrid antibody; antigen; hapten; protein A; protein G; lectin; biotin; avidin; chelating agent; enzyme; enzyme inhibitor; protein receptor; nucleotide hybridizing agent; or a bacteria, virus, Mycoplasmatales, spore, parasite, yeast, or fragment thereof; or combinations thereof.

XVI. Conclusion

In conclusion it can be seen that the present invention provides a sensitive and accurate binding assay technique. While the above is a complete description of specific embodiments of the invention, various modifications and alternatives are possible. Therefore, the above description should not be taken as limiting the scope of the invention which is defined by the claims.

What is claimed is:

1. An interferometer-based system for measuring an analyte, comprising:

an optically transparent substrate comprising (a) an active region having thereon an immobilized substance which specifically binds said analyte and (b) an inactive region which does not bind said analyte;

a light source for outputting a source light beam;

first means for splitting said source light beam into first and second light beams directed along first and second paths, respectively, with said first and second light beams passing through said substrate, said first and second paths having respective first and second optical path lengths;

means for effecting relative movement between said substrate in said first and second paths so that at least one of said first and second light beams is directed through said active region and at least one of said first and second light beams is directed through said inactive region, wherein said first light beam undergoes a phase change relative to said second light beam due to specific binding of said analyte to said active region;

second means for recombining said first and second light beams after said first light beam passes through said active region, said first light beam accumulating a first total phase along said first path between said first means and said second means, said second light beam accumulating a second total phase along said second path between said first means and said second means;

said second means providing at least one recombined beam having and optical power that depends on a difference between said first and second total phases;

optical detection means, coupled to said second means, for converting said at least one recombined beam into at least one electrical signal representing the optical power of said at least one recombined beam;

control means, coupled to at least one of said first and second paths and responsive to a control signal, for modifying the optical path length of at least one of said first and second paths; and third means, responsive to said at least one electrical signal, (a) for generating said control signal so as to maintain a desired relationship between said first and second total phases, and (b) for providing an output signal corresponding to the amount of said analyte bound to said active region based on the phase change produced when said at least one of said first and second light beams passes through said active region and when said at least one of said first and second light beams passes through said inactive region.

2. The system according to claim 1, wherein said means for effecting relative movement causes said first light beam to be alternately passed through said active and said inactive regions.

3. The system according to claim 1, wherein said second light beam is directed to pass through said inactive region.

4. The system according to claim 3, wherein said second light beam is alternately passed through said active and said inactive regions.

5. The system according to claims 1, 2, 3, or 4 wherein said desired relationship is that the first derivative of said at least one electrical signal with respect to said difference between said first and second total phases is a maximum.

6. An interferometer-based binding assay system for measuring a target analyte, comprising:

an optically transparent substrate having (a) plural active regions which specifically bind the target analyte and (b) plural inactive regions which do not bind the target analyte, arranged in a predetermined pattern;

a light source for outputting a source light beam;

first means for splitting said source light beam into first and second light beams directed along first and second paths, respectively, through said substrate, said first and second paths having respective optical first and second path length;

means for moving said substrate relative to said first and second paths so that each of said first and second light beams passes alternately through said active and inactive regions, said first light beam passing through an active region when said second light beam passes through an inactive region, said second light beam passing through an active region when said first light beam passes through an inactive region;

second means for recombining said first and second light beams after said first and second light beams pass through said substrate, said first light beam accumulating a first total phase along said first path between said first means and said second means, said second light beam accumulating a second total phase along said second path between said first means and said second means;

said second means providing first and second recombined beams having respective optical powers that depend on a difference between said first and second total phases; and photodetector means, coupled to said second means, for converting said first and second recombined beams into respective first and second electrical signals representing said optical powers of said first and second recombined beams;

control means, coupled to at least one of said first and second light paths and responsive to a control signal, for modifying the optical path length of at least one of said first and second paths relative to the other; and third means, responsive to said electrical signals, (a) for generating said control signal so as to maintain a desired relationship between said first and second total phases, and (b) for providing an output signal which varies in dependence on the amount of said analyte bound to said active regions.

7. The system according to claim 6 wherein said desired relationship is that the first derivative of a difference between said first and second electrical signals with respect to the difference between said first and second total phases is a maximum.

8. The system according to claim 6, wherein said first means comprises:

a first beamsplitter for transmitting as said first light beam a portion of said source light beam and reflecting as said second light beam a portion of said source light beam; and a first mirror for reflecting one of said first and second light beams toward said substrate.

9. The system according to claim 8, wherein:

said second means comprises, a second mirror for reflecting said first light beam after said first light beam traverses said substrate, a second beamsplitter for transmitting a portion of the first light beam reflected by said second mirror and reflecting a portion of said second light beam after said second light beam passes through said substrate in a first direction to define said first recombined beam, and for reflecting a portion of said first light beam and transmitting a portion of said second light beam in a second direction to define said second recombined beam; and said photodetector means comprises, a first photodetector arranged to intercept light beams transmitted in said first direction by said second means, and a second photodetector arranged to intercept light beams transmitted in said second direction by said second means.

10. The system according to claim 9, wherein:

said third means comprises a differential amplifier having positive and negative inputs coupled to respective outputs of said first and second photodetectors, and servo amplifier means, having a predetermined gain and frequency response, for amplifying an output of said differential amplifier and producing an amplified output; and said control means comprises piezoelectric transducer means driven by an output of said servo amplifier means and coupled to one of said first and second mirrors for controlling positioning of said one of said first and second mirrors so that light is incident on said first and second photodetectors in amounts that are substantially the same.

11. The system according to claim 8, and further comprising:

an auxiliary mirror for reflecting to and through the substrate the second light beam reflected by said first beamsplitter and said first mirror, a second mirror for reflecting the first and second light beams transmitted through said substrate back to said first beamsplitter and to said auxiliary mirror, respectively, the second light beam reflected back to said auxiliary mirror being reflected from said auxiliary mirror to said first mirror and to said photodetector means, the light beam reflected back to said first beamsplitter being reflected by said first beamsplitter to said photodetector means.

12. The system according to claims 7, 8, 9, 10, or 11, wherein said substrate has said active and inactive binding reagent regions arranged as interspersed pluralities of spots disposed in a circle about a rotation axis of said substrate.

13. The system according to claims 7, 8, 9, 10, or 11, wherein said substrate has said active and inactive binding reagent regions arranged as interspersed pluralities of wedges of said substrate.

14. The system according to claim 6, wherein said control means comprises:

a brewster plate inserted in one of said first and second optical paths.

15. The system according to claims 7 or 8, further comprising:

means for producing a synchronization signal in synchronization with said output signal; and lock-in amplifier means having as inputs said synchronization signal and said output signal for producing a filtered signal corresponding to said analyte bound to said active regions.

16. A method of measuring an analyte on a substrate, comprising:

providing an optically transparent substrate comprising (a) an active region with the analyte specifically bound thereto, and (b) an inactive region without the analyte specifically bound thereto;

providing an interferometer having at least two beams travelling along respective beam paths;

inserting the substrate into at least one of the beam paths so as to intercept at least one of the beams;

moving the substrate relative to the interferometer to phase modulate light in the interferometer due to passage of the at least one of the beams through the active region and the inactive region;

measuring a phase change in the at least one of the beams transmitted through the active region due to the analyte specifically bound to the active region and through the inactive region due to any non-specific binding to the inactive region;

controlling the interferometer by modifying at least one of the beam paths so as to maintain a desired phase difference between the two beam paths;

generating an output signal indicative of the amount of analyte bound to the active region based on the measured phase change; and correlating the output signal to the amount of the analyte on the sample.

17. A method of measuring an analyte in a sample, comprising:

contacting the sample with an optically transparent substrate comprising (a) an active region having a substance immobilized thereon which specifically binds the analyte and (b) an inactive region which does not bind the analyte in the sample;

providing an interferometer having at least two beams travelling along respective beam paths;

inserting the substrate into at least one of the beam paths so as to intercept at least one of the beams;

moving the substrate relative to the interferometer to phase modulate light in the interferometer due to passage of the at least one of the beams through the active region and the inactive region;

measuring a phase change in the at least one of the beams transmitted through the active region due to the analyte specifically binding thereto and through the inactive region due to any non-specific binding to the inactive region;

controlling the interferometer by modifying at least one of the beam paths so as to maintain a desired phase difference between the two beam paths;

generating an output signal indicative of the amount of analyte bound to the active region based on the measured phase change; and correlating the output signal to the amount of the analyte in the sample.

* * * * *